United States Patent
Yoshida et al.

(10) Patent No.: US 8,268,356 B2
(45) Date of Patent: Sep. 18, 2012

(54) AQUEOUS FILM COATING SOLUTION, FILM COATED GRANULE AND TABLET USING THE SAME

(75) Inventors: Naoya Yoshida, Tokyo (JP); Yoshihito Yaginuma, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 219 days.

(21) Appl. No.: 12/742,853

(22) PCT Filed: Nov. 12, 2008

(86) PCT No.: PCT/JP2008/070609
§ 371 (c)(1),
(2), (4) Date: May 13, 2010

(87) PCT Pub. No.: WO2009/063916
PCT Pub. Date: May 22, 2009

(65) Prior Publication Data
US 2010/0260839 A1    Oct. 14, 2010

(30) Foreign Application Priority Data

Nov. 16, 2007  (JP) ................................. 2007-297666

(51) Int. Cl.
- *A61K 9/14* (2006.01)
- *A61K 9/16* (2006.01)
- *A61K 9/20* (2006.01)
- *A61K 31/715* (2006.01)
- *C08K 5/11* (2006.01)
- *C08K 5/00* (2006.01)
- *C08K 5/09* (2006.01)
- *C08K 5/05* (2006.01)

(52) U.S. Cl. .......... 424/489; 424/464; 424/497; 514/57; 524/310; 524/312; 524/388; 524/386

(58) Field of Classification Search .................. 424/464, 424/489, 497; 524/413, 310, 312, 388, 297, 524/386; 514/57
See application file for complete search history.

(56) References Cited

U.S. PATENT DOCUMENTS

| | | | |
|---|---|---|---|
| 5,196,203 A | 3/1993 | Boehm | |
| 6,328,994 B1 | 12/2001 | Shimizu et al. | |
| 2002/0142034 A1 | 10/2002 | Shimizu et al. | |
| 2005/0256255 A1 | 11/2005 | Karlsson et al. | |
| 2005/0287211 A1* | 12/2005 | Yoshida et al. | ............... 424/469 |
| 2007/0021391 A1* | 1/2007 | Doi et al. | ....................... 514/114 |
| 2007/0141149 A1 | 6/2007 | Kuhar et al. | |
| 2010/0172978 A1 | 7/2010 | Yaginuma et al. | |
| 2010/0209504 A1 | 8/2010 | Yaginuma et al. | |

FOREIGN PATENT DOCUMENTS

| | | |
|---|---|---|
| EP | 2098250 | 9/2009 |
| JP | 3-002115 | 1/1991 |
| JP | 4-169522 | 6/1992 |
| JP | 6-293635 | 10/1994 |
| JP | 8-109126 | 4/1996 |
| JP | 2000-281564 | 10/2000 |
| JP | 2005-522542 | 7/2005 |
| JP | 3746167 | 2/2006 |
| WO | 2005/060939 | 7/2005 |
| WO | 2008/081891 | 7/2008 |

OTHER PUBLICATIONS

International Preliminary Report on Patentability for PCT/JP2008/070609, mailed Jul. 8, 2010.
International Search Report that issued with respect to PCT/JP2008/070609, mailed Dec. 16, 2008.

\* cited by examiner

*Primary Examiner* — Blessing Fubara
(74) *Attorney, Agent, or Firm* — Greenblum & Bernstein, P.L.C.

(57) ABSTRACT

An object of the present invention is to provide an aqueous film coating solution, and the like, which has good acid resistance and sustained release properties as well as the flexibility suitable for the tablet compression force and are highly productive and cost efficient. The aqueous film coating solution of the present invention comprises an ethyl acrylate/methyl methacrylate copolymer dispersion, a methacrylic acid copolymer LD, a plasticizer, titanium oxide and water, wherein the solid mass ratio of the ethyl acrylate/methyl methacrylate copolymer dispersion, the methacrylic acid copolymer LD, the plasticizer and the titanium oxide is 100:(40 to 100):(5 to 50):(5 to 30) and the solid content thereof is 5 to 20 mass %.

12 Claims, 16 Drawing Sheets

AQUEOUS FILM COATING SOLUTION, FILM COATED GRANULE AND TABLET USING THE SAME

This application is a 371 of PCT/JP2008/070609 filed Nov. 12, 2008.

TECHNICAL FIELD

The present invention relates to aqueous film coating solutions and film coated granules as well as tablets using the same and, in particular, to an aqueous film coating solution preferably used for the purpose of pharmaceutical preparations.

BACKGROUND ART

In the pharmaceutical solid preparations, a sustained release film coating may sometimes be used for the purpose of reducing adverse drug reactions, reducing the dose frequency and enhancing drug effects. In another case, in the oral preparations containing a drug which degrades in a low pH environment, the preparations may be coated with an enteric film for the purpose of protecting the drug from the gastric acid. Accordingly, to sustained release the preparation containing a drug unstable in a low pH environment, it is essential to impart both functions of the protection from the gastric acid and the sustained release properties.

This type of film coating is commonly applied to tablets and granules, but it is mostly used for the spherical granules to control the performance uniformity. Meanwhile, the tablet is the most favored dosage form among patients in the pharmaceutical solid preparations. Thus, to obtain a tablet with controlled performance uniformity, it is desirable to formulate a tablet by adding other excipients to such a film coated granule.

The compression molding using a tableting machine is known as a typical manufacturing technique for formulating tablets. To secure practical production processes, handleability and transportability of the tablet, it is required to enhance the tablet hardness by the compression molding while applying a pressure to some extent. However, when tableting a film coated granule by the compression molding, the film layer (coating layer) is damaged by the pressure applied at the time of the compression molding, whereby the drug release-control performance and acid resistance required to the film layer are often deteriorated.

A variety of methods have been proposed to protect an enteric film layer from the mechanical stress applied during the tablet compression force. For example, a method has been proposed wherein a granule is coated with more than two film layers using two kinds of film coating agents having a film softening temperature difference of 50° C. or more, thereby reducing the film damages during the tablet compression force (e.g., see Patent Document 1). Further, another method has been proposed wherein the inner surface and the outer surface of an enteric film layer are coated with a cellulose-based coating agent to relieve the mechanical stress during the tablet compression force (e.g., see Patent Document 2).

Furthermore, an orally disintegrating tablet and the production method thereof have been proposed wherein a granule is coated with an enteric film coating agent containing a mixture of a methacrylic acid copolymer LD and an ethyl acrylate/methyl methacrylate copolymer dispersion and further coated with a coating layer containing a water soluble sugar alcohol such as mannitol, or the like (e.g., see Patent Document 3). By this technique, it is considered that the rough feeling and uncomfortable feeling is diminished when taking such a tablet and disintegration properties, solubility and acid resistance are considered to be improved.

On the other hand, a method for producing a sustained release tablet has been proposed wherein an elementary granule (a particle containing a drug) is coated by a single film layer using an enteric film coating agent and mixed with a pharmaceutical powder additive to formulate a tablet (e.g., see Patent Document 4).

Moreover, a production process which provides drug effects maintained for 24 hours is proposed (e.g., see Patent Document 5). In this production process, granules are first produced using a small content of a drug, an ethyl acrylate/methyl methacrylate copolymer dispersion, crystalline cellulose, and the like. Subsequently, the obtained granules are coated with a film coating agent independent of the pH of the mixture of a methacrylic acid copolymer LD and the ethyl acrylate/methyl methacrylate copolymer dispersion.

Furthermore, a film coating agent has been proposed wherein a methacrylic acid copolymer LD, an ethyl acrylate/methyl methacrylate copolymer dispersion, and a surfactant are polymerized (e.g., see Patent Document 6).

| Patent Document 1 | Japanese Patent Application Laid-Open No. 8-109126 |
|---|---|
| Patent Document 2 | Japanese Patent Application Laid-Open No. 6-293635 |
| Patent Document 3 | Japanese Patent No. 3746167 |
| Patent Document 4 | Japanese Patent Application Laid-Open No. 4-169522 |
| Patent Document 5 | International publication No. WO2005/060939 |
| Patent Document 6 | National Publication of International Patent Application No. 2005-522542 |

DISCLOSURE OF THE INVENTION

Problems to be Solved by the Invention

However, the methods described in Patent Document 1 and Patent Document 2 require to form a plurality of film layers, thereby complicating the film coating steps and affecting the productivity and cost efficiency. The method described in Patent Document 3 also forms a plurality of film layers to improve the tablet strength and thus decreases the damages to the films at the time of tablet compression force. As a result, the method fails to obviate the complicated film coating steps and deteriorated productivity and cost efficiency described above.

The sustained release tablet obtained by the method described in Patent Document 4 has the structure wherein an elementary granule is coated with a single film layer. However, the tablet still exhibits insufficient acid resistance and sustained release properties which are evident as shown in the tablet dissolution test conducted in examples whereby the drug was dissolved about 50% in the first fluid after 2 hours and about 100% in the second fluid after 30 minutes. Thus, the sustained release tablet was practically useless as an enteric sustained release preparation.

Patent Documents 5 and 6 do not include the study on the film damages at the time of tablet compression force.

Meanwhile, to impart a film layer the property resistant to the mechanical stress applied during the tablet compression force, it seems effective to impart the rubber-like flexibility to the film layer. However, the film coating agents having good flexibility also has high adhesiveness, likely causing the agglomeration of elementary granules (particles containing a drug) and nonuniform film layers during the film coating. Consequently, a reduced tablet yield and impaired film properties tend to be caused. To prevent such an agglomeration of elementary granules and nonuniform film layers, a counteracting technique is known wherein talc is added as an anti-adhesive agent. However, this technique is likely to cause inconveniences such as talc setting in a film coating solution, talc degradation during the film coating, having been always failing to formulate a tablet without sacrificing the productivity and film properties.

As described above, no film coating, which has good acid resistance and sustained release properties as well as flexibility suitable for the tablet compression force and is highly productive and cost efficient, has been known. Similarly, no specific method for actually obtaining such a high performance film coating using a single film layer has not been known.

The present invention is accomplished in the light of these circumstances, and an object of the present invention is to provide an aqueous film coating solution capable of forming a film coating having good acid resistance and sustained release properties as well as flexibility suitable for the tablet compression force and is highly productive and cost efficient, a film coated granule as well as a table using such a granule.

Means for Solving the Problems

The present inventors conducted extensive studies to solve the above problems. As a result, the present inventors found that a film coating having good acid resistance and sustained release properties as well as suitable flexibility for the tablet compression force can be obtained by mixing in a specific ratio an ethyl acrylate/methyl methacrylate copolymer dispersion, a methacrylic acid copolymer LD, a plasticizer and titanium oxide, whereby the present invention is accomplished.

More specifically, the present invention provides the following (1) to (12).

(1) An aqueous film coating solution comprising an ethyl acrylate/methyl methacrylate copolymer dispersion, a methacrylic acid copolymer LD, a plasticizer, titanium oxide and water, wherein the solid mass ratio of the ethyl acrylate/methyl methacrylate copolymer dispersion, the methacrylic acid copolymer LD, the plasticizer and the titanium oxide is 100:(40 to 100):(5 to 50):(5 to 30) and the solid content is 5 to 20 mass %.

(2) The aqueous film coating solution according to the above (1) further comprising an enteric polymer other than the methacrylic acid copolymer LD.

(3) The aqueous film coating solution according to the above (3) wherein the solid mass ratio of the ethyl acrylate/methyl methacrylate copolymer dispersion, the methacrylic acid copolymer LD, the plasticizer, the titanium oxide and the enteric polymer other than the methacrylic acid copolymer LD is 100:(40 to 100):(5 to 50):(5 to 30):(more than 0 and not more than 30).

(4) The aqueous film coating solution according to the above (2) or (3), wherein the average particle size of the enteric polymer is 25 μm or less.

(5) The aqueous film coating solution according to any one of the above (2) to (4), wherein the enteric polymer comprises a methacrylic acid copolymer L.

(6) The film coating solution according to any one of the above (1) to (5), wherein the plasticizer is one or more selected from the group consisting of triethyl citrate, triacetin, glycerin, dibutyl phthalate and propylene glycol.

(7) A film coated granule comprising an elementary granule comprising a drug and a coating layer covering the external surface of the elementary granule, wherein the coating layer comprises an ethyl acrylate/methyl methacrylate copolymer, a methacrylic acid copolymer LD, a plasticizer and titanium oxide, and the solid mass ratio of the ethyl acrylate/methyl methacrylate copolymer, the methacrylic acid copolymer LD, the plasticizer and the titanium oxide is 100:(40 to 100):(5 to 50):(5 to 30).

(8) The film coated granule according to claim 7 wherein the coating layer further comprises an enteric polymer other than the methacrylic acid copolymer LD.

(9) The film coated granule according to the above (8) wherein the solid mass ratio of the ethyl acrylate/methyl methacrylate copolymer, the methacrylic acid copolymer LD, the plasticizer, the titanium oxide and the enteric polymer other than the methacrylic acid copolymer LD is 100: (40 to 100):(5 to 50):(5 to 30):(more than 0 and not more than 30).

(10) The film coated granule according to any one of the above (7) to (9), wherein the plasticizer is one or more selected from the group consisting of triethyl citrate, triacetin, glycerin, dibutyl phthalate and propylene glycol.

(11) The film coated granule according to any one of the above (7) to (10), wherein the elementary granule comprises a spherical nuclear particle comprising 70 mass % or more of crystalline cellulose.

(12) A tablet containing the film coated granule of any one of the above (7) to (11).

Effect of the Invention

According to the present invention, an enteric sustained release film coated granule and tablet with good acid resistance and sustained release properties can be obtained which is capable of gradually releasing a drug when delivered to the intestine but substantially without releasing the drug in the stomach (acidic region). Further, since a film coating having the flexibility suitable for the tablet compression force is obtained, the deterioration of the properties caused by the tablet compression force such as acid resistance, sustained release properties, and the like, can be controlled. Furthermore, the agglomeration of elementary granules and nonuniform film layers during the film coating can be prevented by controlling the development of excessive adhesiveness, thereby enhancing the even more productivity and cost efficiency. Even when the elementary granule has a structure of a single film layer coating, such a high performance film coating can be achieved, thereby even more enhancing the productivity and cost efficiency.

BEST MODE FOR CARRYING OUT THE INVENTION

Figure 1:
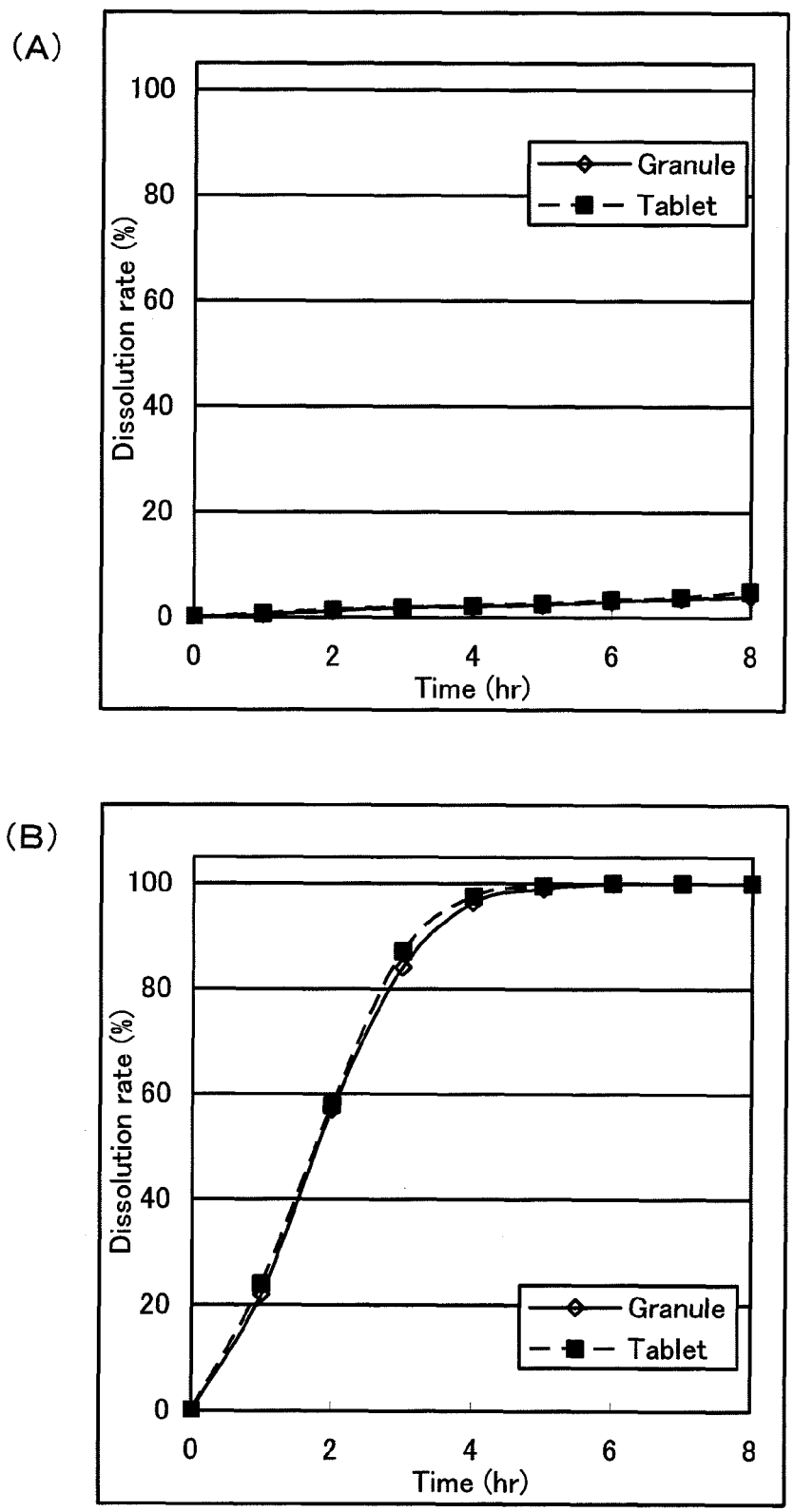
FIG. 1 is a graph showing the time-dependent changes in the drug dissolution rate of the granules and tablets prepared in Examples.

Hereinafter, the embodiments of the present invention are described. The present invention is not limited to these embodiments and can be carried out in various embodiments without departing from the aspect of the invention.

The aqueous film coating solution of the present embodiment (hereinafter also referred to as simply "film coating solution") is an aqueous coating solution which contains at least an ethyl acrylate/methyl methacrylate copolymer dispersion, a methacrylic acid copolymer LD, a plasticizer, titanium oxide and water as essential components with a solid content of 5 to 20 mass %, and is composed of the ethyl acrylate/methyl methacrylate copolymer dispersion (a), the methacrylic acid copolymer LD (b), the plasticizer (c) and the titanium oxide (d) in a solid mass ratio of a:b:c:d=100:(40 to 100):(5 to 50):(5 to 30).

The features of such an aqueous film coating solution are, even used for a single film layer structure, good acid resistance and sustained release properties exhibited without sacrificing the productivity, cost efficiency and film properties. Additionally, another feature of the solution lies in the capability of forming a coating layer (film coating layer) which has the flexibility that protects a film from the damage caused by the mechanical stress during the tablet compression force, good tablet compression force resistance and enteric sustained release properties.

The "acid resistance and sustained release properties" herein indicates the property by which a solid preparation orally administered substantially does not release a drug to the outside in the stomach where is a low pH region but gradually releases the drug when delivered to the intestines where is a high pH region. More specifically, the term means the property that the drug dissolution rate in the "dissolution test first an artificial gastric buffer" (pH 1.2) is about 3% after 3 hours and the drug dissolution rate in the "dissolution test second an artificial intestinal buffer" (pH 6.8) reaches about 100% after 2 to 20 hours as described in the Japanese Pharmacopeia 15th edition (hereinafter referred to as "the Pharmacopeia").

The ethyl acrylate/methyl methacrylate copolymer dispersion is a copolymer dispersion of an ethyl acrylate and methyl methacrylate. The ethyl acrylate/methyl methacrylate copolymer dispersion is, for example, an emulsion of the copolymer resin obtained by polymerizing an ethyl acrylate and methyl methacrylate in water using polyoxyethylene nonylphenyl ether as an emulsifier. The dispersion often contains a small amount of dimethylpolysiloxane. The solid content is preferably 28.1 to 31.5 mass %. A more preferable embodiment of the dispersion is that compliant with the standard for the "ethyl acrylate/methyl methacrylate copolymer dispersion" stipulated in Japanese Pharmaceutical Excipients 2003 (hereinafter referred to as "JPE"). Commercial products such as Eudragit NE30D (Degussa), Kollicoat EMM30D (BASF), and the like, are available.

The methacrylic acid copolymer LD is a copolymer emulsion obtained by polymerizing methacrylic acid and ethyl acrylate in, for example, an aqueous solution of polysorbate 80 and sodium lauryl sulfate. The solid content is preferably 27.0 to 33.0 mass %. A more preferable embodiment of the methacrylic acid copolymer LD is that compliant with the standard for the "methacrylic acid copolymer LD" stipulated in JPE. Commercial products such as Eudragit L30D-55 (Degussa), Kollicoat MAE30DP (BASF), Polyquid PA30S (Sanyo Chemical Industries, Ltd.), and the like, are available.

The plasticizer is a substance which imparts plasticity to a polymer and usually lowers the glass transition point and the softening temperature. Specific examples of the plasticizer include triethyl citrate, triacetin, glycerin, dibutyl phthalate, propylene glycol, and like those listed in JPE. Preferables are triethyl citrate, triacetin, glycerin, dibutyl phthalate and propylene glycol, more preferable are triethyl citrate, triacetin, and the most preferable is triethyl citrate. These are used singly or two or more are used in combination.

The titanium oxide means a titanium dioxide ($TiO_2$) and those compliant with the standard stipulated in the Pharmacopeia are more preferable. Commercial products such as KA-10 (Titan Kogyo, Ltd.), titanium oxide (Toho Titanium Co., Ltd.), and the like, are available.

The solid mass ratio of the above ethyl acrylate/methyl methacrylate copolymer dispersion (a), methacrylic acid copolymer LD (b), plasticizer (c) and titanium oxide (d) described earlier is newly found by the present inventors to attain not only good acid resistance and sustained release properties but also outstanding tablet compression force resistance for the formulation of the film coated granule.

The "tablet compression force resistance" herein means the property bearable against the mechanical stress applied during the tablet compression force. More specifically, the term means that the hardness of the tablet molded by the compression is 50 N or higher and the tensile elongation of a cast film formed using the aqueous film coating solution (methods for forming and measuring are in accordance with the methods described in Examples to be described later) is 150% or higher. The tensile elongation of such a cast film is preferably 200% or higher.

The aqueous film coating solution can be prepared by mixing water and an ethyl acrylate/methyl methacrylate copolymer dispersion (a), a methacrylic acid copolymer LD (b), a plasticizer (c) and titanium oxide (d) and dissolving and/or dispersing. The solid content of the aqueous film coating solution is not limited and may be suitably adjusted in accordance with the purpose of use but is preferably 5 to 20 mass %.

The blending ratio of the ethyl acrylate/methyl methacrylate copolymer dispersion, in the light of imparting the flexibility suitable for the tablet compression force and good tablet compression force resistance and sustained release properties, is preferably 35.7 mass % or higher, more preferably 45 mass % or higher, on a solid basis, to the total solid mass of the aqueous film coating solution. However, the upper limit of the blending amount of the ethyl acrylate/methyl methacrylate copolymer dispersion is not limited, and is preferably 62 mass % or lower in terms of controlling the coating ability affected by the development of excessive adhesiveness.

The blending amount of the methacrylic acid copolymer LD, in the light of imparting good enteric properties, is preferably 18.2 to 47.6 mass % on a solid basis to the total solid mass of the aqueous film coating solution. The blending ratio of the methacrylic acid copolymer LD may suitably be determined in accordance with a desired product design. However, an increased blending ratio of the methacrylic acid copolymer LD is likely to expedite the drug dissolution rate, whereas a decreased blending ratio of the methacrylic acid copolymer LD is likely to delay the dissolution rate. From this viewpoint, the solid mass ratio of the ethyl acrylate/methyl methacrylate copolymer dispersion (a) and the methacrylic acid copolymer LD (b) is (a):(b)=100:(40 to 100), more preferably (a):(b)=100:40 to 90, further preferably (a):(b)=100:(40 to 85).

The blending amount of the plasticizer is preferably 1 to 25 mass % on a solid basis to the total solid mass of the aqueous film coating solution. When the methacrylic acid copolymer LD described earlier is used singly, the film formation properties tend to be poor. However, the addition of such a plasticizer not only enhances the film formation properties but also reinforces the strength of the entire film. The blending ratio of the plasticizer may be suitably determined in accordance with a desired product design. However, an increased blending ratio of the plasticizer is likely to increase adhesiveness, whereas a decreased blending ratio thereof is likely to deteriorate the film formation properties. From this viewpoint, the solid mass ratio of the ethyl acrylate/methyl methacrylate copolymer dispersion (a) and the plasticizer (c) is preferably (a):(c)=100:(5 to 50), more preferably (a):(c)=100:(5 to 30).

The blending amount of the titanium oxide is preferably 1 to 20 mass % on a solid basis to the total solid mass of the aqueous film coating solution. Further, the solid mass ratio of the ethyl acrylate/methyl methacrylate copolymer dispersion (a) and the titanium oxide (d) is (a):(d)=100:(5 to 30). An increased blending ratio of the titanium oxide can decrease the film adhesiveness but tends to reduce the tensile elongation of the cast film. A decreased blending ratio of the titanium oxide can increase the film adhesiveness. From this viewpoint, the solid mass ratio of the ethyl acrylate/methyl methacrylate copolymer dispersion (a) and the titanium oxide (d) is more preferably (a):(d)=100:(5 to 20). When the ethyl acrylate/methyl methacrylate copolymer dispersion described above is used, a film having good flexibility is easily obtained. On the other hand, such a film usually has a high adhesiveness, likely affecting the productivity in the film coating of, in particular, small particles (elementary granules). Titanium oxide has good suspension stability and still has high adhesiveness reducing effects. In viewpoint of enhancing the suspension stability of the aqueous film coating solution and reducing the adhesiveness, it is an essential blending component of the present embodiment.

The aqueous film coating solution described earlier preferably further contains an enteric polymer other than the methacrylic acid copolymer LD (hereinafter referred to simply as "enteric polymer"). The addition of such an enteric polymer enables the adjustment of the dissolution rate in a high pH environment. The enteric polymer herein needs to be adjusted to the particle size well fit in the thickness of the film layer formed by the aqueous film coating solution, and is preferably a powder having an average particle size of 25 μm or smaller, more preferably 20 μm or smaller. The particle size is suitably adjusted by pulverizing using a known apparatus. Examples of such a pulverizer include those having the mechanisms for impact, friction, shear, and the like, and particularly preferable pulverizer is a jet mill. An example of the apparatus used for measuring the average particle size is a laser diffraction scattering particle size distribution analyzer.

Specific examples of the enteric polymer include methacrylic acid copolymer L (tradename: Eudragit L, L100, L100-55, Degussa), hydroxypropyl methylcellulose phthalate acetate succinate (tradename: AQOAT, Shin-Etsu Chemical), carboxy methyl ethyl cellulose (tradename: CMEC, Freund), hydroxypropyl methylcellulose phthalate (tradename: HPMCP, Shin-Etsu Chemical), cellulose acetate phthalate (tradename: CAP, product of Wako Pure Chemical Industries, Ltd.), and the like.

A particularly preferable enteric polymer is methacrylic acid copolymer L. The methacrylic acid copolymer L herein is a white powder copolymer of methacrylic acid and methyl methacrylate, and more specifically those compliant with the standard for the "methacrylic acid copolymer L" stipulated in JPE. Commercial products such as Eudragit L (Degussa), L100 (Degussa), and the like, are easily obtainable.

When the methacrylic acid copolymer L is used as an enteric polymer, the blending amount thereof is, in the light of adjusting the dissolution rate in a high pH environment, preferably 3 to 20 mass % on a solid basis to the total solid mass of the aqueous film coating solution. Further, it is preferable to blend the ethyl acrylate/methyl methacrylate copolymer dispersion (a), the methacrylic acid copolymer LD (b), the plasticizer (c), the titanium oxide (d) and the enteric polymer (e) in a solid mass ratio of (a):(b):(c):(d):(e) is 100:(40 to 100):(5 to 50):(5 to 30):(more than 0 and not more than 30). An increased blending ratio of the enteric polymer can increase the drug dissolution rate, but tends to decrease the tensile elongation of the cast film. A decreased blending ratio of the enteric polymer tends to delay the drug dissolution rate. From these viewpoints, the solid mass ratio of the ethyl acrylate/methyl methacrylate copolymer dispersion (a) and the enteric polymer (e) is preferably (a):(e)=100:(more than 0 and not more than 30), more preferably 100:(10 to 30). A solid mass ratio of the enteric polymer higher than (a):(e)=100:30 expedites the drug dissolution rate, thereby affecting the sustained release properties and the tensile elongation of the cast film. From this viewpoint, the aqueous film coating solution of the present embodiment preferably contains no enteric polymer rather than increasing the solid mass ratio of the enteric polymer to a ratio of higher than (a):(e)=100:30.

Subsequently, the film coated granule is described. The film coated granule of the present embodiment consists of a drug-containing elementary granule and a coating layer covering the external surface of the elementary granule (hereinafter sometimes referred to as "film layer"). The film coated granule of the present embodiment can be obtained, for example, by film-coating an elementary granule containing a drug with the aqueous film coating solution described above by a known method.

The drug-containing elementary granule is not limited, and examples include those prepared by high-speed agitation granulation, fluidized bed granulation, extrusion granulation, extrusion/spherical granulation or a drug layering technique using a nuclear particle, or crystalline drug particle per se, can be used. From viewpoint of obtaining the film coated granule capable of achieving precise drug dissolution control, the elementary granule is particularly preferably a spherical granule prepared by a layering technique. The size of the elementary granule may suitably be determined based on a formulation design concept, but the smaller the better when a tablet formation by the tablet compression force is followed. This is because the smaller size is effective to reduce not only the film damages by the mechanical stress applied during the tablet compression force but also the segregation (disproportionation of the mixing components) during mixing, transporting and tablet compression force compressing powders (elementary granules). More specifically, the average particle size of the elementary granule is preferably 500 μm or less, more preferably 300 μm or less. Further, the lower limit of the average particle size of the elementary granule is preferably 100 μm. The average particle size herein means the value of cumulative 50 mass % based on the undersize cumulative distribution of the particle size measured by a screening method.

Hereinafter, a method for producing an elementary granule by a drug layering technique using a nuclear particle. The layering techniques include a method wherein a drug powder and an aqueous solution of a binder are supplied simultaneously to coat a nuclear particle, a method wherein a suspension of drug particles is supplied for coating, a method wherein a drug-containing aqueous solution is supplied for coating, and the like, and any known method is applicable without limitation. When supplying a drug powder and a binder containing aqueous solution simultaneously, additives in addition to the drug, e.g., excipients, can be used as necessary by mixing with the drug powder. When using a drug containing suspension or aqueous solution, a fluidized bed coating apparatus (sometimes referred to as fluidized-bed-drying machine or fluid-bed-granulating machine) is preferably used.

The nuclear particle used in the drug layering technique is usually pharmaceutically inactive, i.e., those not containing a drug. Specific examples of the nuclear particle include crystalline cellulose, lactose, saccharose, mannitol, corn starch, powdered cellulose, dibasic calcium phosphate, calcium carbonate, low substituted hydroxypropylcellulose, carmellose calcium, partial alpha starch, croscarmellose sodium, crospovidone, carboxy methyl starch, hydroxypropylcellulose, povidone, xanthan gum, compound materials thereof, and the like. Among these, a spherical nuclear particle containing crystalline cellulose is preferably used due to a low agglomeration of the elementary granules during layering. In particular, since it is difficult to carry out the drug layering without agglomerating nuclear particles of 300 μm or smaller, the use of spherical nuclear particle containing crystalline cellulose is preferable from this viewpoint, and the spherical nuclear particles containing 70% or more of the crystalline cellulose is even more preferable. Further, particularly preferable is the spherical nuclear particle made of crystalline cellulose consisting of 100% crystalline cellulose. The "crystalline cellulose" herein means those compliant with the standard for the "crystalline cellulose" of the Japanese Pharmacopeia 15th edition. A specific example of the crystalline cellulose spherical nuclear particle is CELPHERE <registered tradename> (Asahi Kasei Chemicals Corporation). Further, a specific example of sugar nuclear particle is Nonpareil <registered tradename> (Freund), and the like.

The drug is hereinafter described. The drug is a substance used for treating, preventing or diagnosing diseases of human and animals, not an apparatus or a machine. Specific examples thereof include oral administration drugs such as fever reducing/pain relieving/antiinflammatory drug, hypnotic drug, stimulant, pediatric analgesic, stomachic, antacid, digestant, cordial, arrhythmic drug, depressor, vasodilator, diuretic drug, antiulcer drug, intestinal regulator, osteoporosis drug, antitussive/expectorant, antiasthmatic drug, antimicrobial agent, urinary frequency improving agent, nourishment tonic, vitamins, and the like. These drugs may be used singly or two or more may be used in combination.

Among these, the drug unstable in the stomach and yet required long-lasing drug effects is preferably used. Specific examples include natural penicillin antibiotic (benzylpenicillin), lansoprazole, pancreatin, phenylpropanolamine hydrochloride, phenytoin, calcium disodium edetate, omeprazole, L-ethyl cysteine hydrochloride, pyridoxal phosphate, ethionamide, and the like.

The film coating to the elementary granule using the aqueous film coating solution, that is, the formation of a coating layer, is not limited, and any known technique is applicable without limitation. For example, the film coating can be carried out, using a similar apparatus as used in a drug laying technique, by spraying the aqueous film coating solution to the surface of the elementary granule and drying the solution, followed by repeating the procedures as necessary. In such a film coating, it is preferable to use a fluidized bed apparatus of spout bed type equipped with an internal guide tube (Wurster column), a fluidized bed apparatus of tumbling fluidized bed type equipped with a rotary mechanism at the bottom, or the like. For the supply (spray) of the aqueous film coating solution, any known technique suitable with an apparatus used such as top spray, bottom spray, side spray, tangential spray, or the like, can be selected as necessary. During supplying (spraying) the aqueous film coating solution, it is preferable to stir with a propeller, or the like, as necessary, to prevent titanium oxide from settling in the aqueous film coating solution. After completing the spray, the air flow and temperature are adjusted suitably to dry the film coated granules. Thus, the film coated granules wherein the external surface of the elementary granules is coated with a coating layer having the ethyl acrylate/methyl methacrylate copolymer, the methacrylic acid copolymer LD, the plasticizer and the titanium oxide in a solid mass ratio of 100:(40 to 100):(5 to 50):(5 to 30). After forming the coating layer, the layer is preferably subjected to curing from a viewpoint of enhancing the film forming properties.

The amount of coating by the film coating (film coating amount) may suitably be determined based on a formulation design concept in consideration of the size of elementary granule, drug amount to be supported (contained), drug solubility to water, and the like. The total mass of the coating layer is preferably about 10 to about 50 mass %, more preferably 15 to 30 mass %, to the total mass of the drug-containing elementary granule. When an elementary granule having an average particle size of 100 μm or smaller, for example, is used or when a drug easily soluble in water is used, the drug dissolution rate tends to be comparatively expedited. In such an instance, the total mass of the coating layer is suitably adjusted to about 15 to about 80 mass % to accord with an intended dissolution properties. An example of the method for adjusting the dissolution properties includes the following method. More specifically, for a sustained release preparation, the time for a drug to be 100% released is first predetermined. Then, to gradually release the drug by the predetermined time, the blending amounts of the methacrylic acid copolymer LD and the enteric polymer, which are the enteric bases in the film coating, the film coating amount and the film layer thickness are varied. However, the method for adjusting the dissolution properties is not limited thereto.

The dissolution properties of the film coated granule is evaluated, as described earlier, using the Pharmacopeia "dissolution test first an artificial gastric buffer" (pH 1.2) and Pharmacopeia "dissolution test second an artificial gastric buffer" (pH 6.8).

The tablet is subsequently described. After eliminating agglomerated particles (coarse particles) using a sieve, or the like, as necessary, the obtained film coated granules can be formulated into tablets by the tablet compression force singly or in mixture with other granules or other film coated granules, or the like. As in the routine tableting, pharmaceutical additives such as pharmaceutically acceptable drugs, excipients, disintegrants, binders, lubricants, etc., and compressing powders are optionally added to formulate an enteric sustained release granule-containing tablet. For example, by using suitably selected excipient, disintegrant, binder, and the like, the film coated granule can be formulated into an orally disintegrating tablet. For the compressing powder, it is preferable to select a material having high compression molding properties, suitable disintegrating properties and least likely to damage the film coated granules. A specific example of the material having high compression molding properties is crystalline cellulose.

The tablet compression force may be carried out by a common method using a rotary tablet compression force machine, and is not limited. From viewpoint of preventing the segregation of the film coated granules and other pharmaceutical additive powders, it is preferable to perform the tablet compression force using a force feeder. The content of the film coated granule in a tablet ranges preferably from 5 to 70 mass %, more preferably 10 to 50 mass %, from viewpoint of the balance between the molding properties and disintegrating properties.

EXAMPLES

Hereinafter, the present invention is described in detail in reference with Examples and Comparative Examples, but is not limited thereto. The part number and % in Examples, and the like, indicate mass unless otherwise stated.

The measuring methods of the physical properties in Examples and Comparative Examples are together described below.

<Tensile Elongation Test of Cast Film>
(1) The aqueous film coating solution was put into a polyethylene petri dish (diameter 11.3 cm) so as to give a dried film thickness of 0.2 to 0.4 mm.
(2) The petri dish was put in an oven and dried at 40° C. for 10 hours and further dried at 80° C. for 1 hour.
(3) The petri dish was taken out from the oven and cooled at room temperature.
(4) The dried film in the petri dish was taken out, cut out to a size of 10 mm×30 mm to obtain the cast film for a tensile elongation test.
(5) Using a tensile elongation test (a creep meter, RE-33005 model, product of Yamaden Co., Ltd.), the obtained cast film was inserted and fixed between the sheet-like tensile chucks (upright type) so that the distance to be measured was 10 mm. The cast film was pulled apart at a speed of 0.5 mm/sec and the stretch rate at the cast film broke was measured.

<Drug Dissolution Test>
The drug dissolution test was carried out in accordance with General Tests, "Dissolution Test", in the Pharmacopeia. Using "Method 2" (Puddle method) described in the Pharmacopeia at the number of the puddle revolution of 100 rpm, the "dissolution test 1st an artificial gastric buffer (pH 1.2)" (hereinafter also referred to as "1st fluid") and the "dissolution test 2nd an artificial intestinal buffer (pH 6.8)" (hereinafter also referred to as "2nd fluid") described in the Pharmacopeia were used as the test fluids.

<Average Particle Size [μm] of Film Coated Granules, Etc.>
20 g of a sample was sieved for 15 minutes to measure the particle size distribution with the JIS standard sieve (JIS Z8001) using a Ro-tap sieve shaker (Sieve Shaker A model, Taira Koseisakusho, Ltd.). The average particle size is a particle size at a cumulative 50 mass % in the undersize cumulative distribution.

<Measurement of Granule Yield (%)>
The yield of the film coated granule is divided by the total amount of raw materials used (the sum of the elementary granule mass and the solid mass of the aqueous film coating solution) and expressed in mass %.

<Measurement of Granule Agglomeration Rate (%)>
The agglomerates of the elementary granules obtained by the layering or of the film coated granules obtained by the film coating were sieved to remove. The mass of the granules (agglomerates) which did not pass through the sieve was divided by the total amount of the elementary granule or the total amount of the film coated granule, and expressed in mass %.

<Measurement of Table Hardness>
The tablet hardness was automatically measured by setting tablets in a tablet hardness meter (TS-75N, Freund) and the average value of ten tablets was given as the tablet hardness.

<Measurement of Tablet Disintegration Time>
In accordance with the Disintegration Time stipulated in the Pharmacopeia, six tablets were placed in a disintegration test apparatus (NT-40HS, Toyama Sangyo K.K.) to test the disintegrating properties in water. The time required for the tablet to lose the original form until no residue was identified was measured, and the average value of the six tables was given as the disintegration time.

Example 1

<Preparation of Elementary Granule>
20.0 kg of a crystalline cellulose spherical nuclear particle (tradename: CELPHERE CP-305, average particle size: 385 μm, Asahi Kasei Chemicals Corporation) was placed in a tumbling fluidized bed coater (Multiplex MP-25 model, Powlex Corporation). Using 10 mass % of riboflavin (Daiichi Fine Chemical Co., Ltd.) as a drug, 3 mass % of povidone (PVP-K30, ISP Ltd.) as a binder and a layering solution composed of 87 mass % of purified water, the above nuclear particles were subjected to the layering under the following conditions. The thus obtained layered particles were sieved using a sieve having an opening of 600 μm, and 20.35 kg of an elementary granule [G1] which passed through the sieve with the opening was obtained.

| | |
|---|---:|
| (1) Air supply temperature: | 75° C. |
| (2) Air discharge temperature: | 40 to 45° C. |
| (3) Air flow volume: | 8.0 m³/min |
| (4) Number of rotor rotation: | 240 rpm |
| (5) Spray air supply pressure: | 0.6 MPa |

| (6) Spray air volume: | 400 N/min |
| (7) Spray nozzle size: | 2.2 mm |
| (8) Amount of spray layering solution: | 120 g/min |
| (9) Amount of layering solution: | 2000 g |
| (10) Drying: | until air discharge temperature reaches 50° C. |

<Preparation of Aqueous Film Coating Solution>

By the following formula, an aqueous film coating solution [L1] was prepared wherein an ethyl acrylate/methyl methacrylate copolymer dispersion [a], a methacrylic acid copolymer LD dispersion [b], a triethyl citrate [c], a titanium oxide [d] and purified water were contained in a solid content of 17 mass %.

Eudragit NE30D (Degussa) was used as the ethyl acrylate/methyl methacrylate copolymer dispersion [a], Eudragit L30D55 (Degussa) as the methacrylic acid copolymer LD dispersion [b], (Tokyo Chemical Industry Co., Ltd.) as the triethyl citrate, and NA61 (Toho Titanium Co., Ltd.) as the titanium oxide [d] were used. The solid mass ratio of these components was a:b:c:d=40:35:15:10 (=100:87.5:37.5:25.2). The tensile elongation of the cast film formed using the aqueous film coating solution [L1] was 199%.

<Production of Film Coated Granule>

Subsequently, 700 g of the elementary granule [G1] was placed in a fluidized bed coater equipped with the following Wurster column. The aqueous film coating solution [L1] was sprayed onto the surface of the elementary granules and dried, whereby the coating (film coating) was done. Thereafter, the film coated elementary granules were sieved using a sieve having an opening of 600 μm to obtain film coated granules [F1] which passed through the sieve with the opening. The film coating conditions are as follows.

| (1) Apparatus used: | GPCG1 model (Glatt GmbH) |
| (2) Air flow volume: | 84 to 90 m³/h |
| (3) Air supply temperature: | 60° C. |
| (4) Air discharge temperature: | 40 to 45° C. |
| (5) Film coating solution amount: | 820 g |
| (6) Spray speed of film coating solution: | 6.3 to 8.2 g/min |
| (7) Spray air pressure: | 0.16 MPa |

The coated film amount of the obtained film coated granule [F1] was 20 mass %, and the average particle size was 443 μm (the film thickness was about 20.3 μm). The yield was 90.7% and the agglomeration rate (the ratio of coarse particles of 600 μm or larger) was 8.8%.

The aqueous coated granule [F1] had riboflavin dissolution rates of 1.8% in the 1st fluid after 3 hours and 57.0% in the 2nd fluid after 2 hours, 96.3% after 4 hours and 100% after 6 hours.

Tablet Production

Then, the film coated granule [F1], crystalline cellulose (tradename: Ceolus PH-200, Asahi Kasei Chemicals Corporation), and partial alpha starch (tradename: PCS PC-10, Asahi Kasei Chemicals Corporation) were mixed in a mass ratio of 50:40:10. The obtained mixture was subjected to the tablet compression force using an AT tablet compression force machine (AIKOH ENGINEERING) to produce a 500 mg tablet [T1] containing the film coated granules. The tablet compression force herein was carried out using a flat mortar and pestle having a diameter of 11.3 mm at a compression pressure of 7 kN. The obtained 500 mg tablet [T1] had a tablet hardness of 150 N and an integration time of 75 seconds.

The 500 mg tablet [T1] had riboflavin dissolution rates of 1.9% in the 1st fluid after 3 hours and 57.8% in the 2nd fluid after 2 hours, 97.5% after 4 hours and 100% after 6 hours. More specifically, the 500 mg tablet [T1] had not only good acid resistance and sustained release properties but also the drug dissolution pattern substantially equivalent to that of the pre-compressed film coated granule [F1], whereby the property deterioration otherwise caused by the tablet compression force was controlled. FIG. 1 shows the time-dependent changes in the drug dissolution rate of the granules and tablets. (A) shows the time-dependent changes in the drug dissolution rate in the 1st fluid and (B) shows the same in the 2nd fluid.

Example 2

By the following formula, an aqueous film coating solution [L2] was prepared wherein an ethyl acrylate/methyl methacrylate copolymer dispersion [a], a methacrylic acid copolymer LD dispersion [b], a triethyl citrate [c], a titanium oxide [d], a methacrylic acid copolymer L [e] and purified water were contained in a solid content of 17 mass %.

Eudragit L100 (Degussa) was crushed to an average particle size of 20 μm using a jet mill pulverizer to use as the methacrylic acid copolymer L [e], and the same materials as in Example 1 were used as other components [a] to [d]. The solid mass ratio of these components was a:b:c:d:e=45:30:5:10:10 (=100:66.7:11.1:22.2:22.2). The tensile elongation of the cast film formed using the aqueous film coating solution [L2] was 213%.

Next, a film coated granule [F2] was produced in the same manner as in Example 1 except that the aqueous film coating solution [L2] was used in place of the aqueous film coating solution [L1].

The coated film amount of the obtained film coated granule [F2] was 20 mass %, and the average particle size was 449 μm (the film thickness was about 23.3 μm). The yield was 94.4% and the agglomeration rate (the ratio of coarse particles of 600 μm or larger) was 6.8%.

The coated granule [F2] had riboflavin dissolution rates of 0.8% in the 1st fluid after 3 hours and 65.1% in the 2nd fluid after 2 hours, 78.8% after 4 hours, 85.7% after 6 hours, 91.4% after 8 hours and 95.6% after 10 hours.

Subsequently, a 500 mg tablet [T2] was produced in the same manner as in Example 1 except that the film coated granule [F2] was used in place of the film coated granule [F1]. The obtained 500 mg tablet [T2] had a tablet hardness of 168 N and an integration time of 89 seconds.

Figure 2:
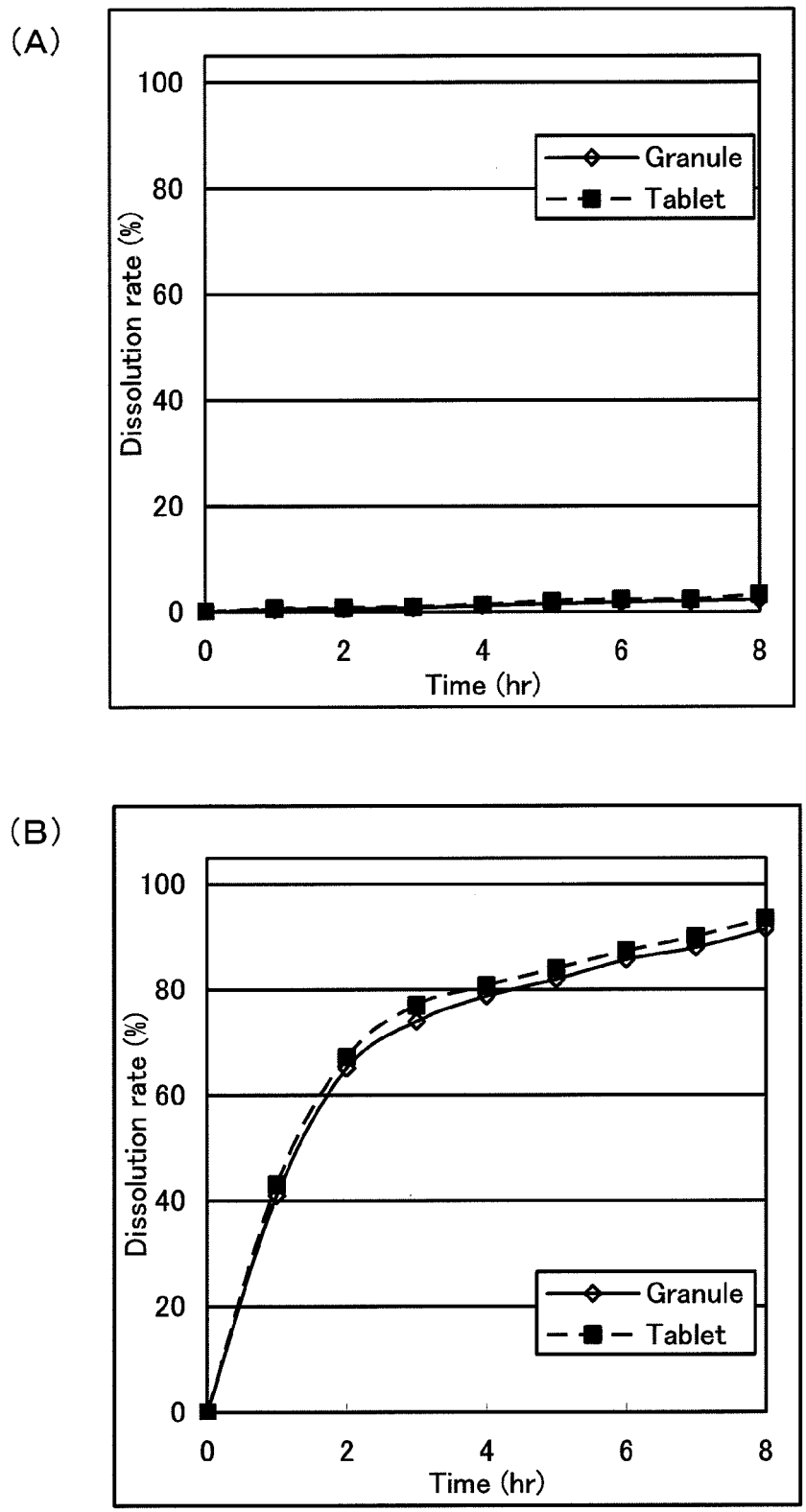
FIG. 2 is a graph showing the time-dependent changes in the drug dissolution rate of the granules and tablets prepared in Examples.

The 500 mg tablet [T2] had riboflavin dissolution rates of 1.2% in the 1st fluid after 3 hours and 67.2% in the 2nd fluid after 2 hours, 80.8% after 4 hours, 87.3% after 6 hours, 93.5% after 8 hours and 98.9% after 10 hours. More specifically, the 500 mg tablet [T2] had not only good acid resistance and sustained release properties but also the drug dissolution pattern substantially equivalent to that of the pre-compressed film coated granule [F2], whereby the property deterioration otherwise caused by the tablet compression force was controlled. FIG. 2 shows the time-dependent changes in the drug dissolution rate of the granules and tablets. (A) shows the time-dependent changes in the drug dissolution rate in the 1st fluid and (B) shows the same in the 2nd fluid.

Example 3

A film coating solution [L3] having a solid content of 17 mass % was prepared in the same manner as in Example 1 except that the solid mass ratio of the blending components was a:b:c:d=60:25:7.5:7.5 (=100:41.6:12.5:12.5). The tensile elongation of the aqueous film coating solution [L3] was 443%.

Next, a film coated granule [F3] was produced in the same manner as in Example 1 except that the aqueous film coating solution [L3] was used in place of the aqueous film coating solution [L1].

The coated film amount of the obtained film coated granule [F3] was 20 mass %, and the average particle size was 454 μm (the film thickness was about 25.8 μm). The yield was 92.8% and the agglomeration rate (the ratio of coarse particles of 600 μm or larger) was 10.2%.

The film coated granule [F3] had riboflavin dissolution rates of 0.7% in the 1st fluid after 3 hours and 26.3% in the 2nd fluid after 2 hours, 61.5% after 4 hours and 75.3% after 6 hours, 83.6% after 8 hours and 89.6% after 10 hours.

Subsequently, a 500 mg tablet [T3] was produced in the same manner as in Example 1 except that the film coated granule [F3] was used in place of the film coated granule [F1]. The obtained 500 mg tablet [T3] had a tablet hardness of 225 N and an integration time of 125 seconds.

Figure 3:
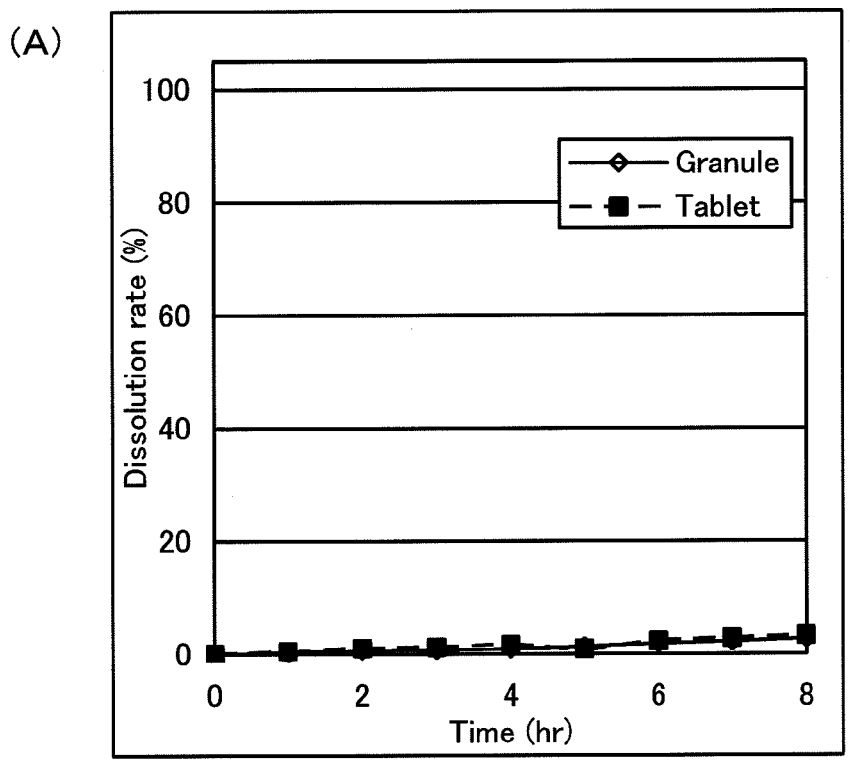
FIG. 3 is a graph showing the time-dependent changes in the drug dissolution rate of the granules and tablets prepared in Examples.
Figure 3:
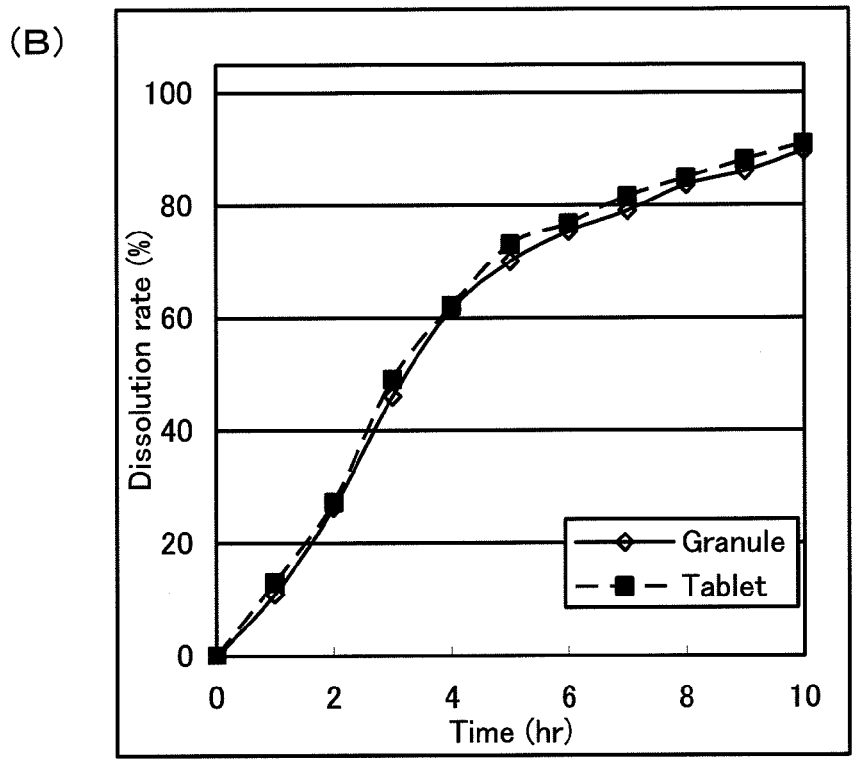

The 500 mg tablet [T3] had riboflavin dissolution rates of 0.8% in the 1st fluid after 3 hours and 27.2% in the 2nd fluid after 2 hours, 62.1% after 4 hours, 76.7% after 6 hours, 84.8% after 8 hours and 90.9% after 10 hours. More specifically, the 500 mg tablet [T3] had not only good acid resistance and sustained release properties but also the drug dissolution pattern substantially equivalent to that of the pre-compressed film coated granule [F3], whereby the property deterioration otherwise caused by the tablet compression force was controlled. FIG. 3 shows the time-dependent changes in the drug dissolution rate of the granules and tablets. (A) shows the time-dependent changes in the drug dissolution rate in the 1st fluid and (B) shows the same in the 2nd fluid.

Example 4

20.37 kg of an elementary granule [G2] was obtained in the same manner as in Example 1 except that a crystalline cellulose spherical nuclear particle (tradename: CELPHERE CP-102, average particle diameter: 160 μm, Asahi Kasei Chemicals Corporation) was used in place of CELPHERE CP-305 and further a sieve having an opening of 300 μm.

Next, a film coated granule [F4] was produced in the same manner as in Example 2 except that the elementary granule [G2] was used in place of the elementary granule [G1].

The coated film amount of the obtained film coated granule [F4] was 20 mass %, and the average particle size was 201 μm (the film thickness was about 17.5 μm). The yield was 92.8% and the agglomeration rate (the ratio of coarse particles of 300 μm or larger) was 7.8%.

The coated granule [F4] had riboflavin dissolution rate of 1.9% in the 1st fluid after 3 hours and 55.9% in the 2nd fluid after 2 hours, 87.6% after 4 hours and 100% after 6 hours.

Subsequently, a 500 mg tablet [T4] was produced in the same manner as in Example 1 except that the film coated granule [F4] was used in place of the film coated granule [F1]. The obtained 500 mg tablet [T4] had a tablet hardness of 195 N and an integration time of 112 seconds.

Figure 4:
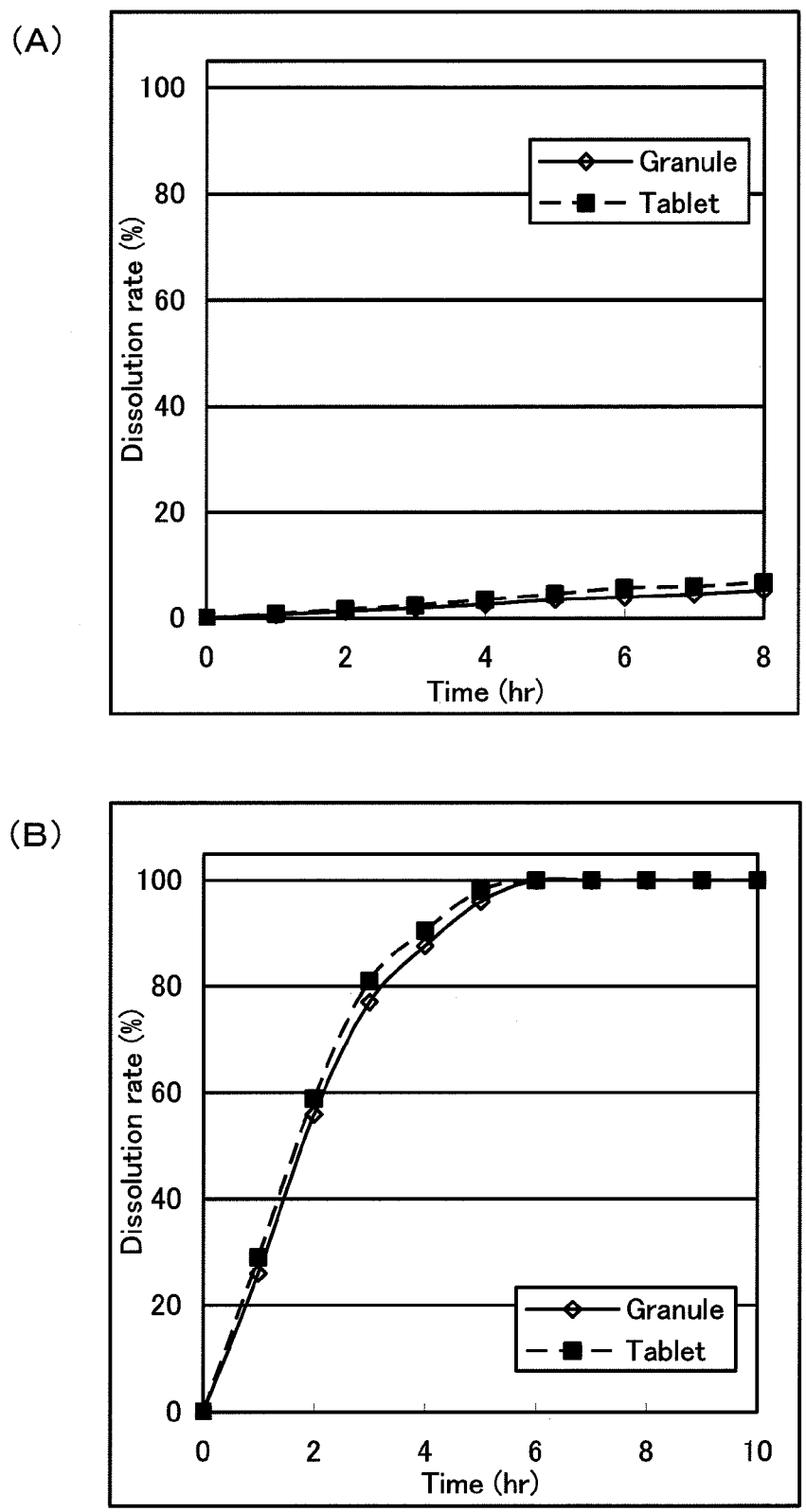
FIG. 4 is a graph showing the time-dependent changes in the drug dissolution rate of the granules and tablets prepared in Examples.

The dissolution rate of riboflavin from the 500 mg tablet [T4] was 2.1% in the 1st fluid after 3 hours and 58.9% in the 2nd fluid after 2 hours, 90.5% after 4 hours and 100% after 6 hours. More specifically, the 500 mg tablet [T4] had not only good acid resistance and sustained release properties but also the drug dissolution pattern substantially equivalent to that of the pre-compressed film coated granule [F4], whereby the property deterioration otherwise caused by the tablet compression force was controlled. FIG. 4 shows the time-dependent changes in the drug dissolution rate of the granules and tablets. (A) shows the time-dependent changes in the drug dissolution rate in the 1st fluid and (B) shows the same in the 2nd fluid.

Example 5

An aqueous film coating solution [L4] having a solid content of 5 mass % was prepared in the same manner as in Example 1 except that the solid content was 5 mass %. The tensile elongation of the cast film formed using the aqueous film coating solution [L4] was 180%.

Next, a film coated granule [F5] was produced in the same manner as in Example 1 except that the aqueous film coating solution [L4] was used in place of the aqueous film coating solution [L1].

The coated film amount of the obtained film coated granule [F5] was 20 mass %, and the average particle size was 440 μm (the film thickness was about 18.8 μm). The yield was 93.5% and the agglomeration rate (the ratio of coarse particles of 600 μm or larger) was 1.7%.

The film coated granule [F5] had riboflavin dissolution rates of 1.5% in the 1st fluid after 3 hours and 56.2% in the 2nd fluid after 2 hours, 95.1% after 4 hours and 100.0% after 6 hours.

Subsequently, a 500 mg tablet [T5] was produced in the same manner as in Example 1 except that the film coated granule [F5] was used in place of the film coated granule [F1]. The obtained 500 mg tablet [T5] had a tablet hardness of 155 N and an integration time of 70 seconds.

Figure 5:
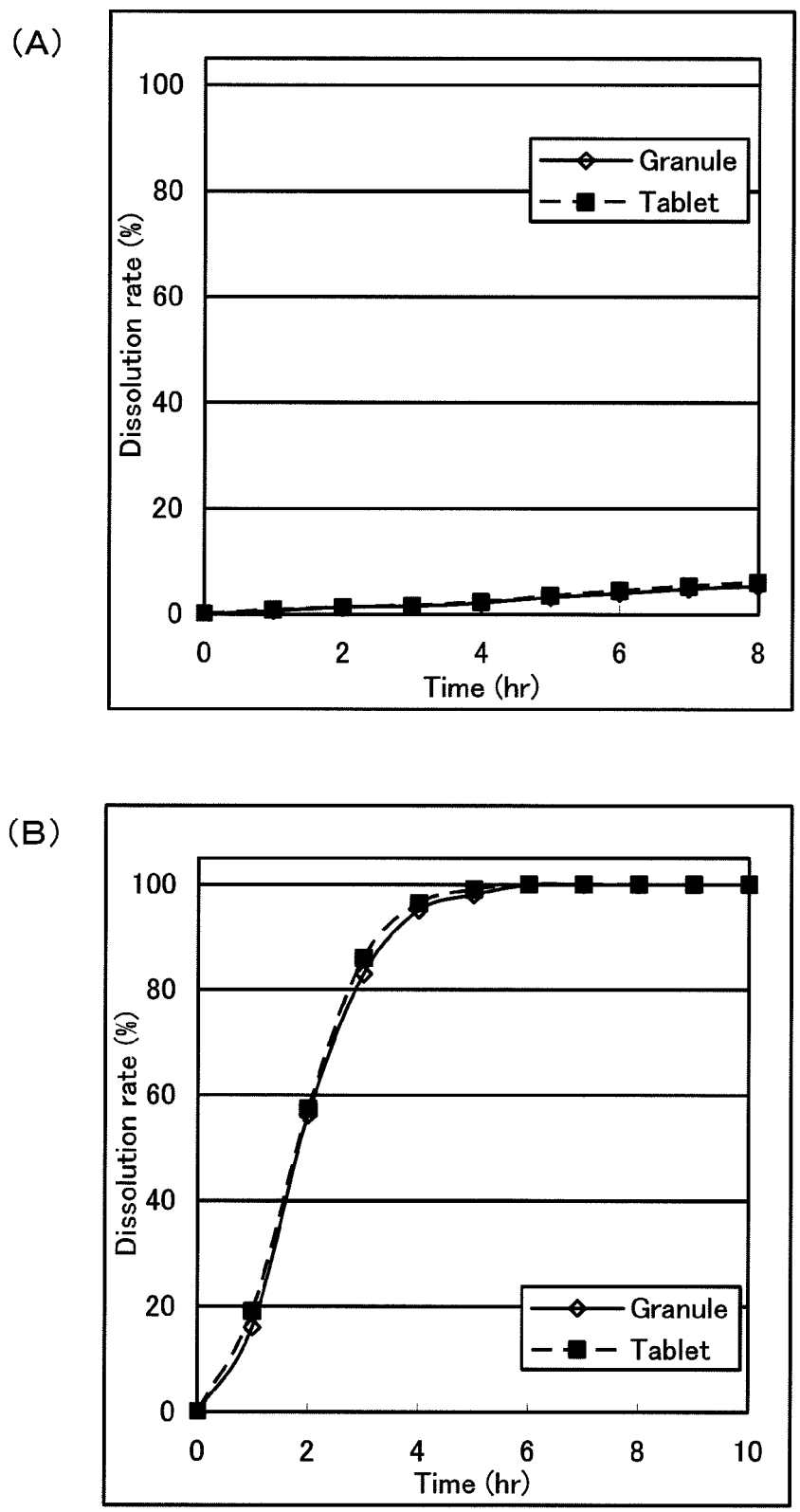
FIG. 5 is a graph showing the time-dependent changes in the drug dissolution rate of the granules and tablets prepared in Examples.

The 500 mg tablet [T5] had riboflavin dissolution rates of 1.61% in the 1st fluid after 3 hours and 57.3% after the 2nd fluid in 2 hours, 96.3% after 4 hours and 100.0% after 6 hours. More specifically, the 500 mg tablet [T5] had not only good acid resistance and sustained release properties but also the drug dissolution pattern substantially equivalent to that of the pre-compressed film coated granule [F5], whereby the property deterioration otherwise caused by the tablet compression force was controlled. FIG. 5 shows the time-dependent changes in the drug dissolution rate of the granules and tablets. (A) shows the time-dependent changes in the drug dissolution rate in the 1st fluid and (B) shows the same in the 2nd fluid.

Example 6

An aqueous film coating solution [L5] having a solid content of 20 mass % was prepared in the same manner as in Example 4 except that the solid content was 20 mass %. The tensile elongation of the cast film formed using the aqueous film coating solution [L5] was 210%.

Next, a film coated granule [F6] was obtained in the same manner as in Example 4 except that the aqueous film coating solution [L5] was used in place of the aqueous film coating solution [L1].

The coated film amount of the obtained film coated granule [F6] was 20 mass %, and the average particle size was 206 μm (the film thickness was about 20.0 μm). The yield was 90.1% and the agglomeration rate (the ratio of coarse particles of 600 μm or larger) was 10.8%.

The film coated granule [F6] had riboflavin dissolution rates of 1.9% in the 1st fluid after 3 hours and 53.5% in the 2nd fluid after 2 hours, 86.9% after 4 hours and 100.0% after 6 hours.

Subsequently, a 500 mg tablet [T6] was produced in the same manner as in Example 1 except that the film coated granule [F6] was used in place of the film coated granule [F1]. The obtained 500 mg tablet [T6] had a tablet hardness of 191 N and an integration time of 120 seconds.

Figure 6:
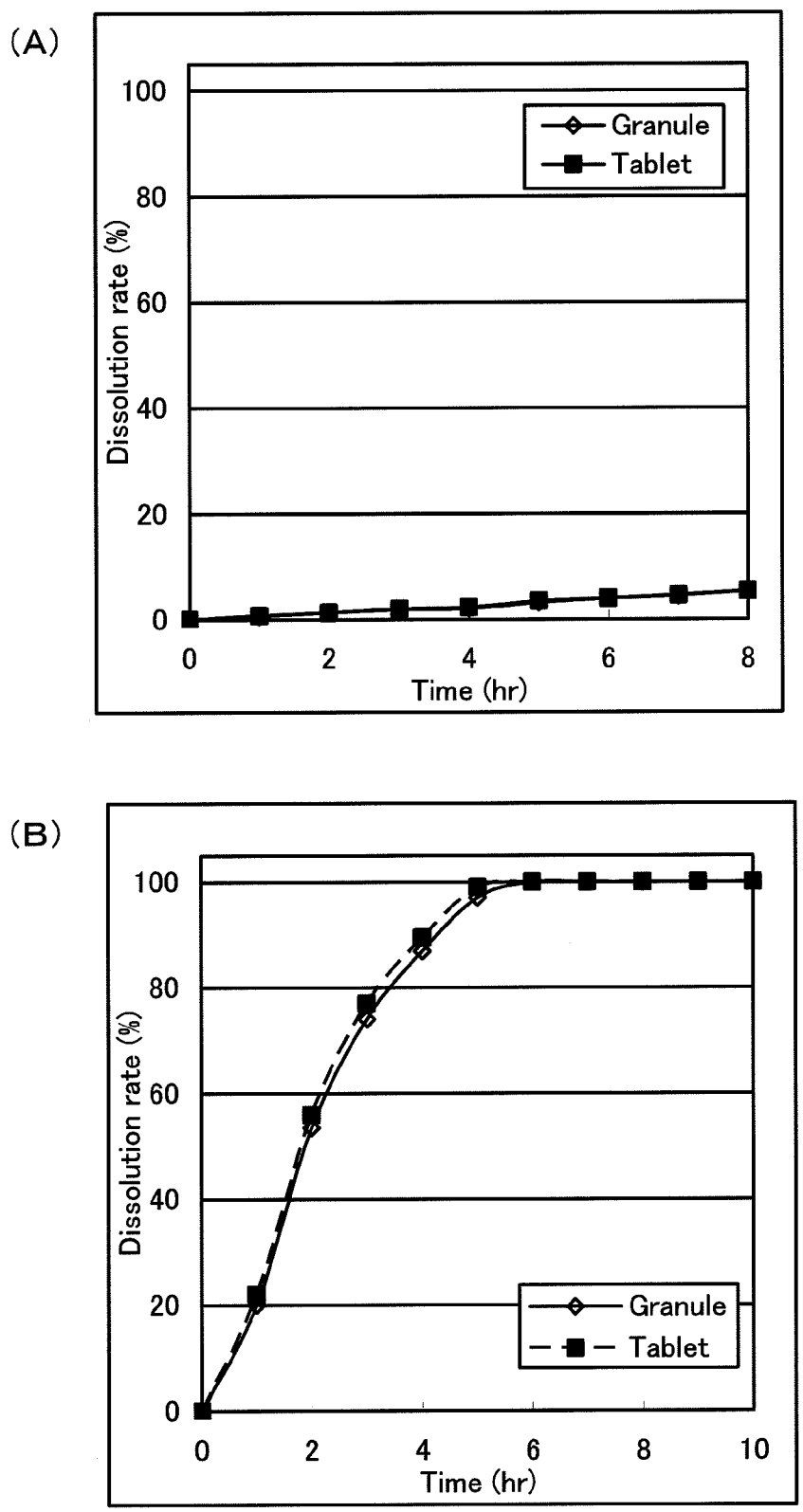
FIG. 6 is a graph showing the time-dependent changes in the drug dissolution rate of the granules and tablets prepared in Examples.

The 500 mg tablet [T6] had riboflavin dissolution rates of 2.0% in the 1st fluid after 3 hours and 55.9% in the 2nd fluid after 2 hours, 89.4% after 4 hours and 100.0% after 6 hours. More specifically, the 500 mg tablet [T6] had not only good acid resistance and sustained release properties but also the drug dissolution pattern substantially equivalent to that of the pre-compressed film coated granule [F6], whereby the property deterioration otherwise caused by the tablet compression force was controlled. FIG. 6 shows the time-dependent changes in the drug dissolution rate of the granules and tablets. (A) shows the time-dependent changes in the drug dissolution rate in the 1st fluid and (B) shows the same in the 2nd fluid.

Example 7

A film coating solution [L6] having a solid content of 17 mass % was prepared in the same manner as in Example 1 except that the solid mass ratio of the blending components was a:b:c:d=43.1:37.7:16.2:3 (=100:87.5:37.5:7). The tensile elongation of the cast film formed using the aqueous film coating solution [L6] was 245%.

Next, a film coated granule [F7] was produced in the same manner as in Example 1 except that the aqueous film coating solution [L6] was used in place of the aqueous film coating solution [L1].

The coated film amount of the obtained film coated granule [F7] was 20 mass %, and the average particle size was 444.4 μm (the film thickness was about 21.0 μm). The yield was 88.2% and the agglomeration rate (the ratio of coarse particles of 600 μm or larger) was 11.6%.

The film coated granule [F7] had riboflavin dissolution rates of 1.1% in the 1st fluid after 3 hours and 72.3% in the 2nd fluid after 2 hours, 94.7% after 4 hours and 100% after 6 hours.

Subsequently, a 500 mg tablet [T7] was produced in the same manner as in Example 1 except that the film coated granule [F7] was used in place of the film coated granule [F1]. The obtained 500 mg tablet [T7] had a tablet hardness of 175 N and an integration time of 90 seconds.

Figure 7:
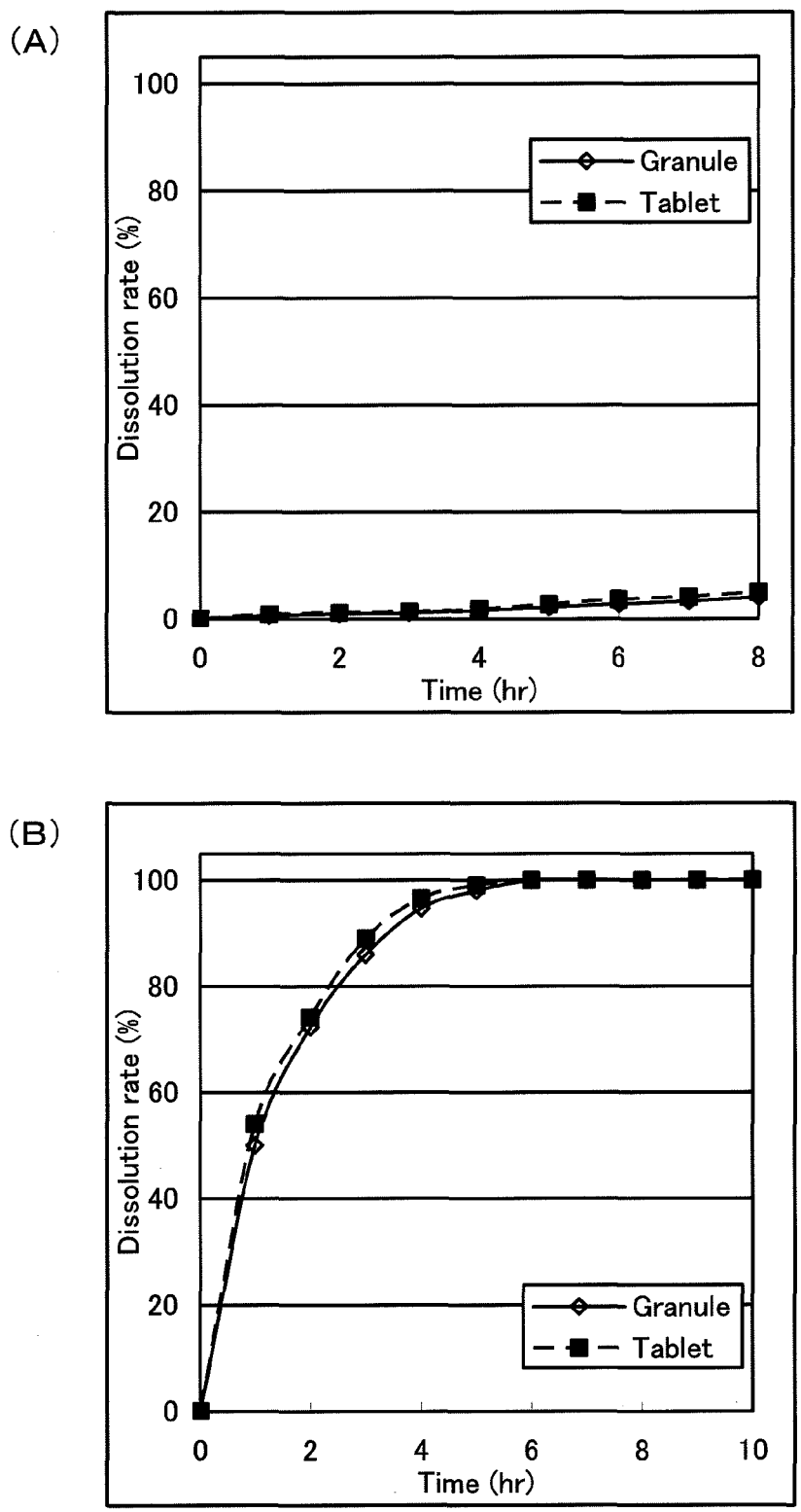
FIG. 7 is a graph showing the time-dependent changes in the drug dissolution rate of the granules and tablets prepared in Examples.

The 500 mg tablet [T7] had riboflavin dissolution rates of 1.3% in the 1st fluid after 3 hours and 74.1% in the 2nd fluid after 2 hours, 96.5% after 4 hours and 100% after 6 hours. More specifically, the 500 mg tablet [T7] had not only good acid resistance and sustained release properties but also the drug dissolution pattern substantially equivalent to that of the pre-compressed film coated granule [F7], whereby the property deterioration otherwise caused by the tablet compression force was controlled. FIG. 7 shows the time-dependent changes in the drug dissolution rate of the granules and tablets. (A) shows the time-dependent changes in the drug dissolution rate in the 1st fluid and (B) shows the same in the 2nd fluid.

Example 8

An aqueous film coating solution [L7] having a solid content of 17 mass % was prepared in the same manner as in Example 2 except that the solid mass ratio of the blending components was a:b:c:d:e=53.8:22.6:3.8:13.4:6.4 (=100:42:7:25:12). The tensile elongation of the cast film formed using the aqueous film coating solution [L7] was 410%.

Next, a film coated granule [F8] was produced in the same manner as in Example 2 except that the aqueous film coating solution [L7] was used in place of the aqueous film coating solution [L2].

The coated film amount of the obtained film coated granule [F8] was 20 mass %, and the average particle size was 464 μm (the film thickness was about 30.8 μm). The yield was 90.5% and the agglomeration rate (the ratio of coarse particles of 600 μm or larger) was 13.0%.

The film coated granule [F8] had riboflavin dissolution rates of 0.9% in the 1st fluid after 3 hours and 40.6% in the 2nd fluid after 2 hours, 75.3% after 4 hours and 84.5% after 6 hours and 100% after 8 hours.

Subsequently, a 500 mg tablet [T8] was produced in the same manner as in Example 2 except that the film coated granule [F8] was used in place of the film coated granule [F1]. The obtained 500 mg tablet [T8] had a tablet hardness of 200 N and an integration time of 110 seconds.

Figure 8:
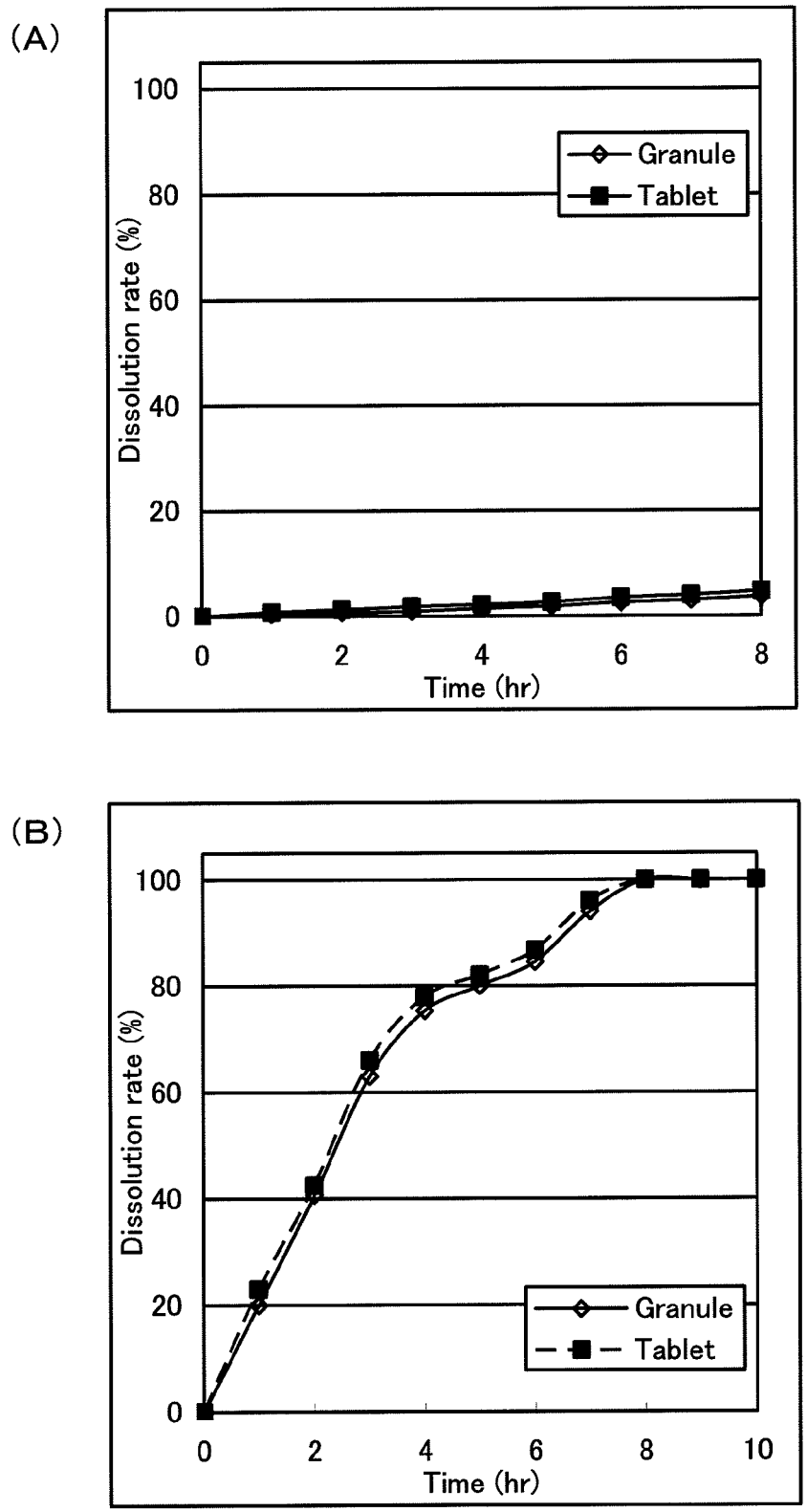
FIG. 8 is a graph showing the time-dependent changes in the drug dissolution rate of the granules and tablets prepared in Examples.

The 500 mg tablet [T8] had riboflavin dissolution rates of 1.8% in the 1st fluid after 3 hours and 42.4% in the 2nd fluid after 2 hours, 77.9% after 4 hours, 86.7% after 6 hours and 100% after 8 hours. More specifically, the 500 mg tablet [T8] had not only good acid resistance and sustained release properties but also the drug dissolution pattern substantially equivalent to that of the pre-compressed film coated granule [F8], whereby the property deterioration otherwise caused by the tablet compression force was controlled. FIG. 8 shows the time-dependent changes in the drug dissolution rate of the granules and tablets. (A) shows the time-dependent changes in the drug dissolution rate in the 1st fluid and (B) shows the same in the 2nd fluid.

Example 9

An aqueous film coating solution [L8] having a solid content of 17 mass % was prepared in the same manner as in Example 1 except that the solid mass ratio of the blending components was a:b:c:d=38.7:33.8:17.8:9.7 (=100:87.5:46:25). The tensile elongation of the cast film formed using the aqueous film coating solution [L8] was 165%.

Next, a film coated granule [F9] was produced in the same manner as in Example 1 except that the aqueous film coating solution [L8] was used in place of the aqueous film coating solution [L1].

The coated film amount of the obtained film coated granule [F9] was 20 mass %, and the average particle size was 430 μm (the film thickness was about 13.8 μm). The yield was 96.8% and the agglomeration rate (the ratio of coarse particles of 600 μm or larger) was 1.5%.

The film coated granule [F9] had riboflavin dissolution rates of 1.0% in the 1st fluid after 3 hours and 81.0% in the 2nd fluid after 2 hours, 96.7% after 4 hours and 100% after 6 hours.

Subsequently, a 500 mg tablet [T9] was produced in the same manner as in Example 1 except that the film coated granule [F9] was used in place of the film coated granule [F1]. The obtained 500 mg tablet [T9] had a tablet hardness of 120 N and an integration time of 65 seconds.

Figure 9:
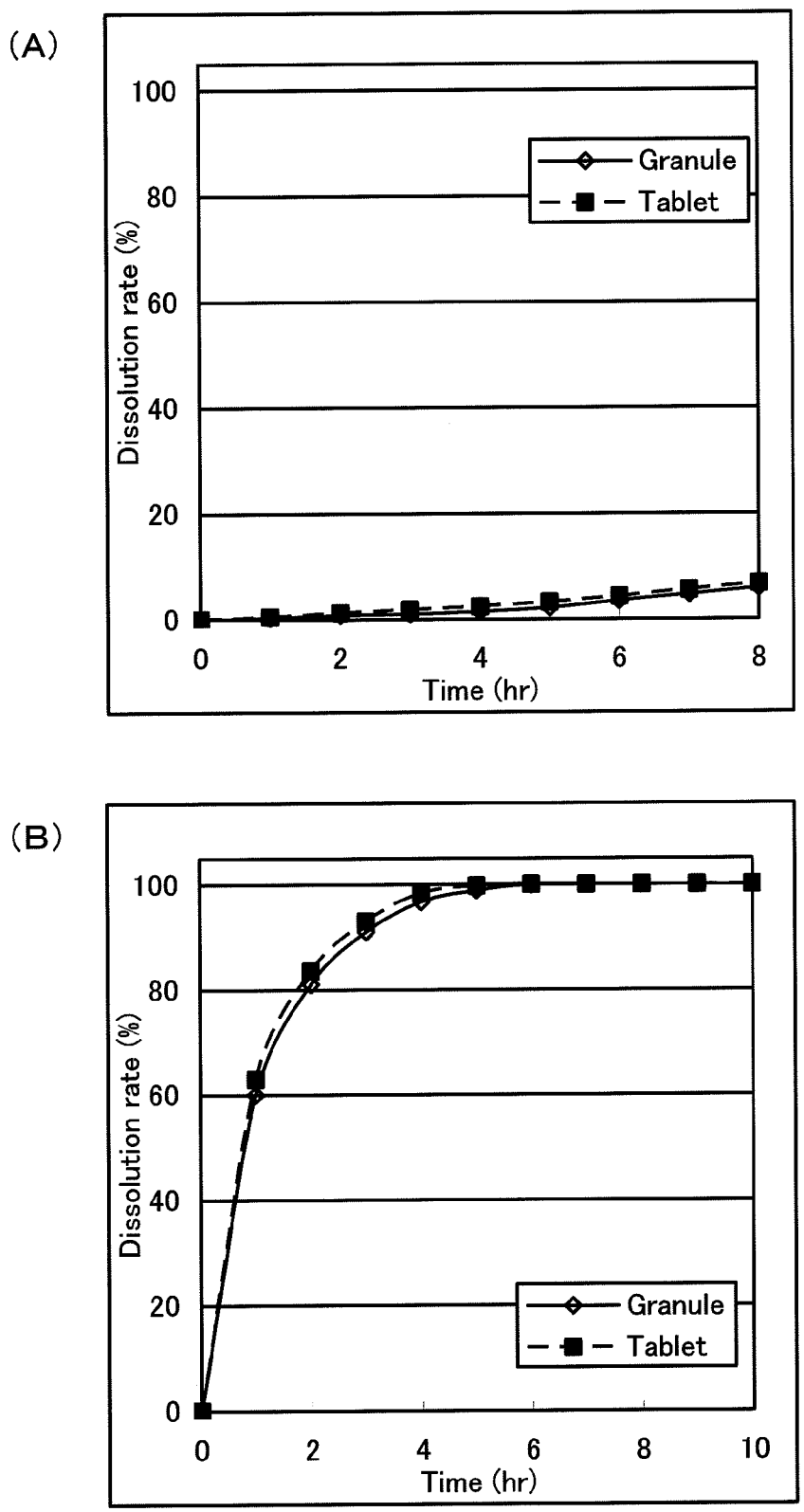
FIG. 9 is a graph showing the time-dependent changes in the drug dissolution rate of the granules and tablets prepared in Examples.

The 500 mg tablet [T9] had riboflavin dissolution rates of 1.6% in the 1st fluid after 3 hours and 83.5% in the 2nd fluid after 2 hours, 98.3% after 4 hours and 100% after 6 hours. More specifically, the 500 mg tablet [T9] had not only good acid resistance and sustained release properties but also the drug dissolution pattern substantially equivalent to that of the pre-compressed film coated granule [F9], whereby the property deterioration otherwise caused by the tablet compression force was controlled. FIG. 9 shows the time-dependent changes in the drug dissolution rate of the granules and tablets. (A) shows the time-dependent changes in the drug dissolution rate in the 1st fluid and (B) shows the same in the 2nd fluid.

Example 10

19.55 kg of an elementary granule [G3] was obtained in the same manner as in Example 1 except that Sulpyrine (Daiichi Fine Chemical Co., Ltd.), a water soluble drug, was used in place of riboflavin as the drug.

Next, a film coated granule [F10] was produced in the same manner as in Example 1 except that the elementary granule [G3] was used in place of the elementary granule [G1].

The coated film amount of the obtained film coated granule [F10] was 20 mass %, and the average particle size was 450 μm (the film thickness was about 23.8 μm). The yield was 87.8% and the agglomeration rate (the ratio of coarse particles of 600 μm or larger) was 9.7%.

The coated granule [F10] had Sulpyrine dissolution rates of 2.4% in the 1st fluid after 3 hours and 100.0% in the 2nd fluid after 2 hours.

Subsequently, a 500 mg tablet [T10] was produced in the same manner as in Example 1 except that the film coated granule [F10] was used in place of the film coated granule [F1]. The obtained 500 mg tablet [T10] had a tablet hardness of 125 N and an integration time of 60 seconds.

Figure 10:
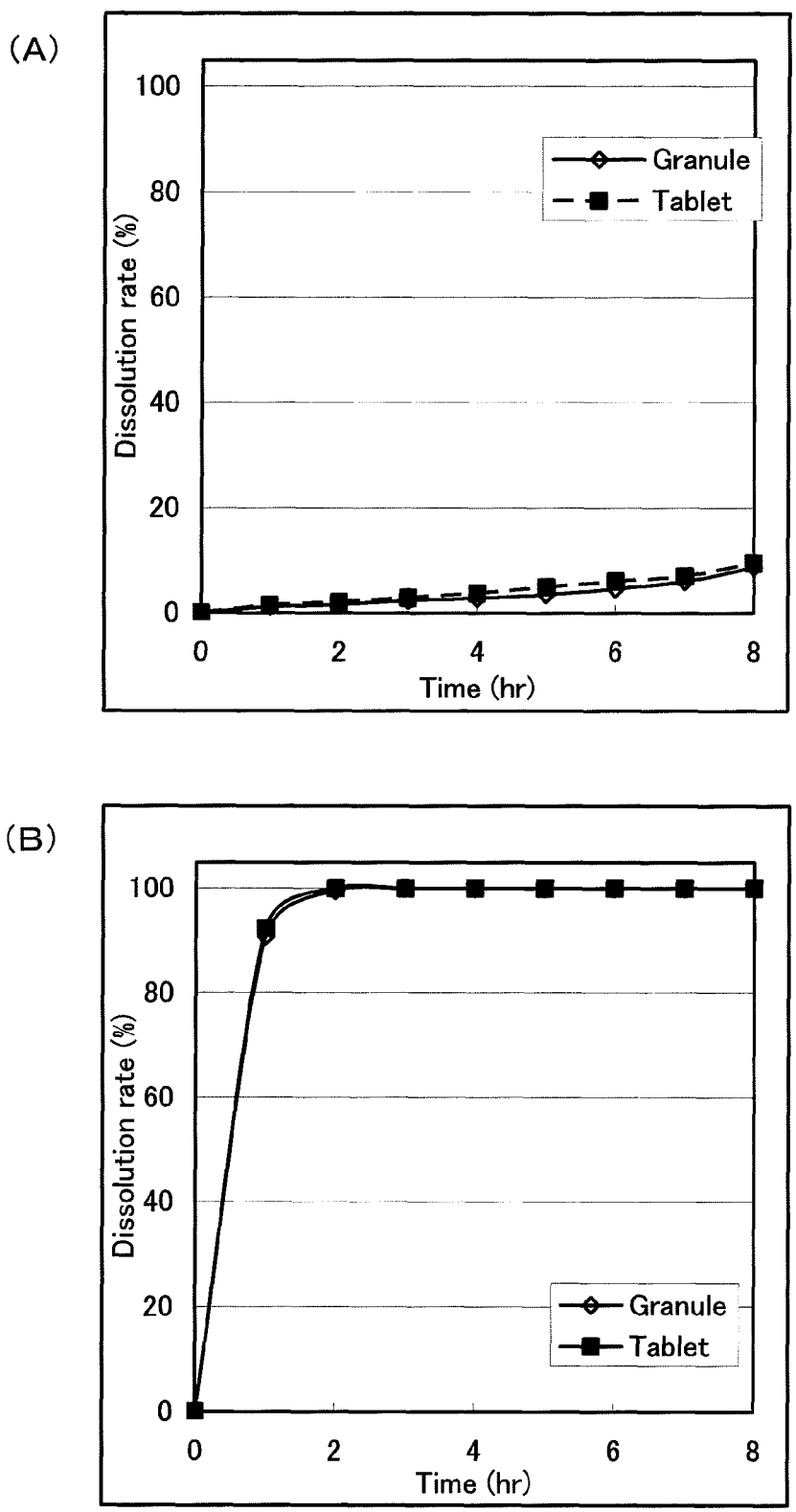
FIG. 10 is a graph showing the time-dependent changes in the drug dissolution rate of the granules and tablets prepared in Examples.

The 500 mg tablet [F10] had Sulpyrine dissolution rates of 2.9% in the 1st fluid after 3 hours and 100% in the 2nd fluid after 2 hours. More specifically, the 500 mg tablet [T10] had not only good acid resistance and sustained release properties but also the drug dissolution pattern substantially equivalent to that of the pre-compressed film coated granule [F10], whereby the property deterioration otherwise caused by the tablet compression force was controlled. FIG. 10 shows the time-dependent changes in the drug dissolution rate of the granules and tablets. (A) shows the time-dependent changes in the drug dissolution rate in the 1st fluid and (B) shows the same in the 2nd fluid.

Example 11

A film coating solution [RL3] having a solid content of 17 mass % was prepared in the same manner as in Example 2 except that the solid mass ratio of the blending components was a:b:c:d:e=40:25:5:10:20 (=100:62.5:12.5:25.0:50.0). The tensile elongation of the cast film formed using the aqueous film coating solution [RL3] was 118%.

Next, a film coated granule [RF3] was produced in the same manner as in Example 1 except that the film coating solution [RL3] was used in place of the aqueous film coating solution [L1].

The coated film amount of the obtained film coated granule [RF3] was 20 mass %, and the average particle size was 461 μm (the film thickness was about 29.3 μm). The yield was 93.8% and the agglomeration rate (the ratio of coarse particles of 600 μm or larger) was 5.5%.

The film coated granule [RF3] had riboflavin dissolution rates of 7.2% in the 1st fluid after 3 hours and 73.1% in the 2nd fluid after 2 hours, 96.4% after 4 hours and 100% after 6 hours.

Subsequently, a 500 mg tablet [RT3] was produced in the same manner as in Example 1 except that the film coated granule [RF3] was used in place of the film coated granule [F1]. The obtained 500 mg tablet [RT3] had a tablet hardness of 138 N and an integration time of 92 seconds.

Figure 11:
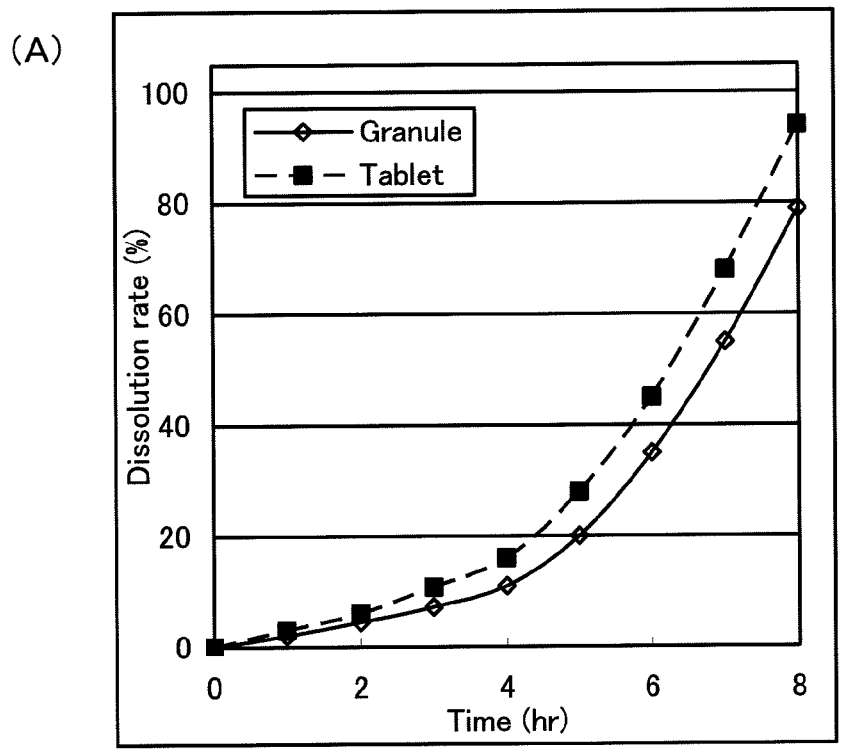
FIG. 11 is a graph showing the time-dependent changes in the drug dissolution rate of the granules and tablets prepared in Examples.
Figure 11:
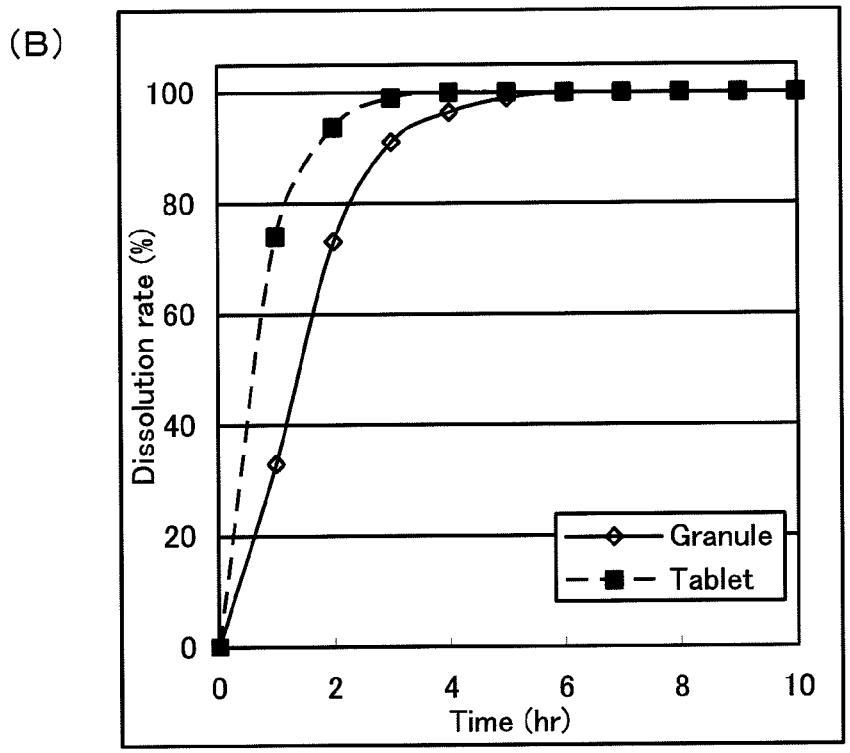

The 500 mg tablet [RT3] had riboflavin dissolution rates of 10.8% in the 1st fluid after 3 hours and 93.7% in the 2nd fluid after 2 hours, 100% after 4 hours and 100% after 6 hours. FIG. 11 shows the time-dependent changes in the drug dissolution rate of the granules and tablets. (A) shows the time-dependent changes in the drug dissolution rate in the 1st fluid and (B) shows the same in the 2nd fluid.

In Example 11, the film coating solution [RL3] containing a considerably large amount of the methacrylic acid copolymer L [e] was used. For this reason, the film coated granule [RF3] and the 500 mg tablet [RT3] had drug dissolutions of 3% or more in the 1st fluid after 3 hours. Further, the drug dissolutions were expedited before and after the tablet compression force which resulted in increased drug dissolutions of 3% or more.

Comparative Example 1

A film coating solution [RL1] having a solid content of 17 mass % was prepared in the same manner as in Example 2 except that the solid mass ratio of the blending components was a:b:c:d:e=30:45:7:8:10 (=100:150:23.3:26.7:33.3). The tensile elongation of the cast film formed using the aqueous film coating solution [RL1] was 94%.

Next, a film coated granule [RF1] was produced in the same manner as in Example 1 except that the film coating solution [RL1] was used in place of the aqueous film coating solution [L1].

The coated film amount of the obtained film coated granule [RF1] was 20 mass %, and the average particle size was 438 μm (the film thickness was about 17.8 μm). The yield was 94.3% and the agglomeration rate (the ratio of coarse particles of 600 μm or larger) was 6.8%.

The film coated granule [RF1] had riboflavin dissolution rates of 7.2% in the 1st fluid after 3 hours and 75.2% in the 2nd fluid after 2 hours, 98.0% after 4 hours and 100% after 6 hours.

Subsequently, a 500 mg tablet [RT1] was produced in the same manner as in Example 1 except that the film coated granule [RF1] was used in place of the film coated granule [F1]. The obtained 500 mg tablet [RT1] had a tablet hardness of 126 N and an integration time of 75 seconds.

Figure 12:
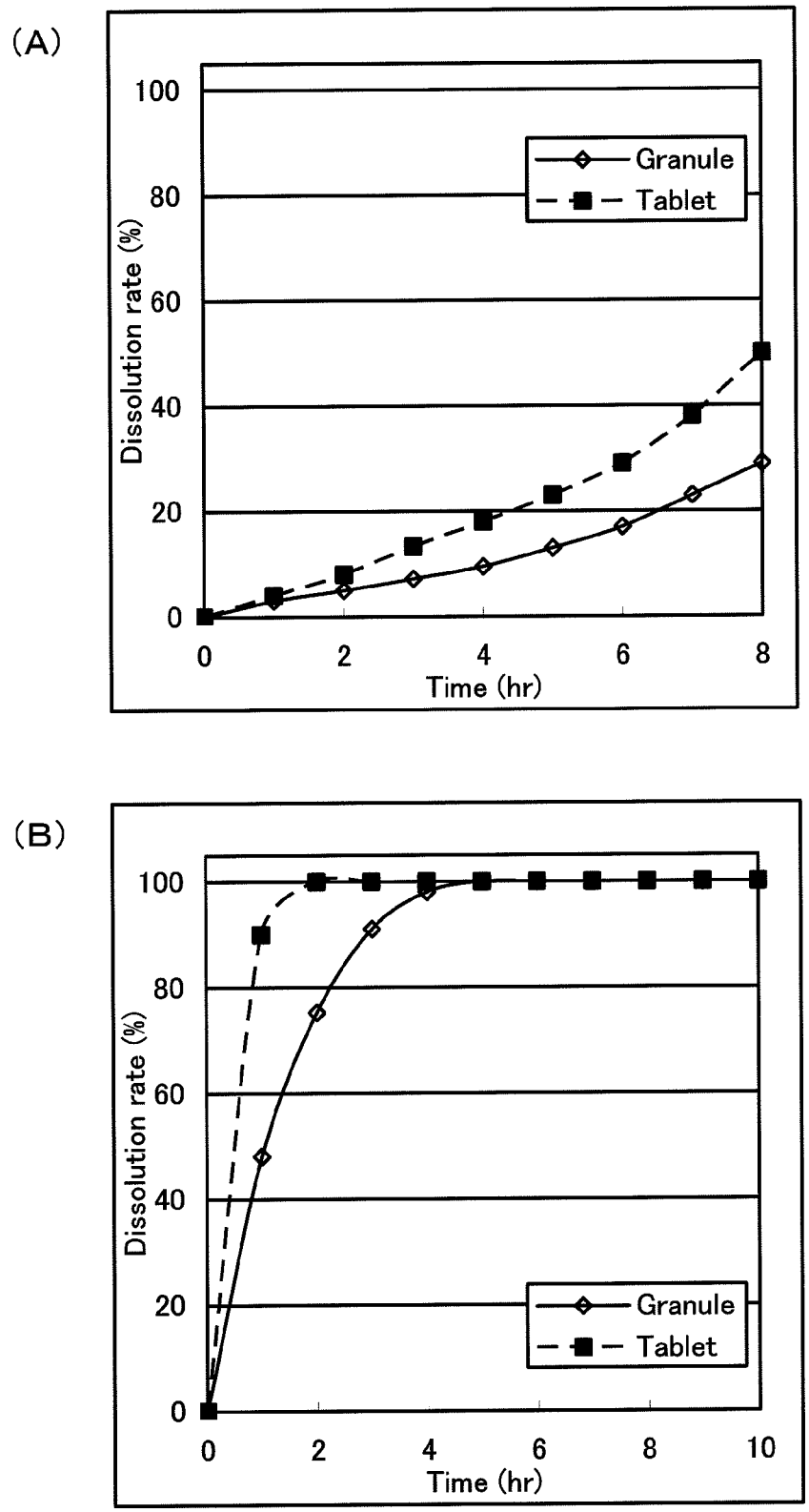
FIG. 12 is a graph showing the time-dependent changes in the drug dissolution rate of the granules and tablets prepared in Comparative Examples.

The 500 mg tablet [RT1] had riboflavin dissolution rates of 13.3% in the 1st fluid after 3 hours and 100% in the 2nd fluid after 2 hours, 100% after 4 hours and 100% after 6 hours. FIG. 12 shows the time-dependent changes in the drug dissolution rate of the granules and tablets. (A) shows the time-dependent changes in the drug dissolution rate in the 1st fluid and (B) shows the same in the 2nd fluid.

In Comparative Example 1, the film coating solution [RL1] was used wherein the blending ratio of the ethyl acrylate/methyl methacrylate copolymer dispersion [a] was lower than the methacrylic acid copolymer LD dispersion [b]. For this reason, the film coated granule [RF1] and the 500 mg tablet [RT1] had drug dissolutions of 3% or more in the 1st fluid after 3 hours. Further, the drug dissolutions were expedited before and after the tablet compression force which resulted in increased drug dissolutions of 3% or more.

Comparative Example 2

A film coating solution [RL2] having a solid content of 17 mass % was prepared in the same manner as in Example 1 except that the solid mass ratio of the blending components was a:b:c:d=65:20:5:10 (=100:30.7:7.8:15.4). The tensile elongation of the cast film formed using the aqueous film coating solution [RL2] was 650%.

Next, a film coated granule [RF2] was produced in the same manner as in Example 1 except that the film coating solution [RL2] was used in place of the aqueous film coating solution [L1].

The coated film amount of the obtained film coated granule [RF2] was 20 mass %, and the average particle size was 458 μm (the film thickness was about 27.8 μm). The yield was 78.6% and the agglomeration rate (the ratio of coarse particles of 600 μm or larger) was 29.5%.

The film coated granule [RF2] had riboflavin dissolution rates of 0.6% in the 1st fluid after 3 hours and 31.3% in the 2nd fluid after 2 hours, 43.0% after 4 hours, 55.6% after 6 hours, 62.5% after 8 hours and 68.2% after 10 hours.

Subsequently, a 500 mg tablet [RT2] was produced in the same manner as in Example 1 except that the film coated granule [RF2] was used in place of the film coated granule [F1]. The obtained 500 mg tablet [RT2] had a tablet hardness of 185 N and an integration time of 180 seconds.

Figure 13:
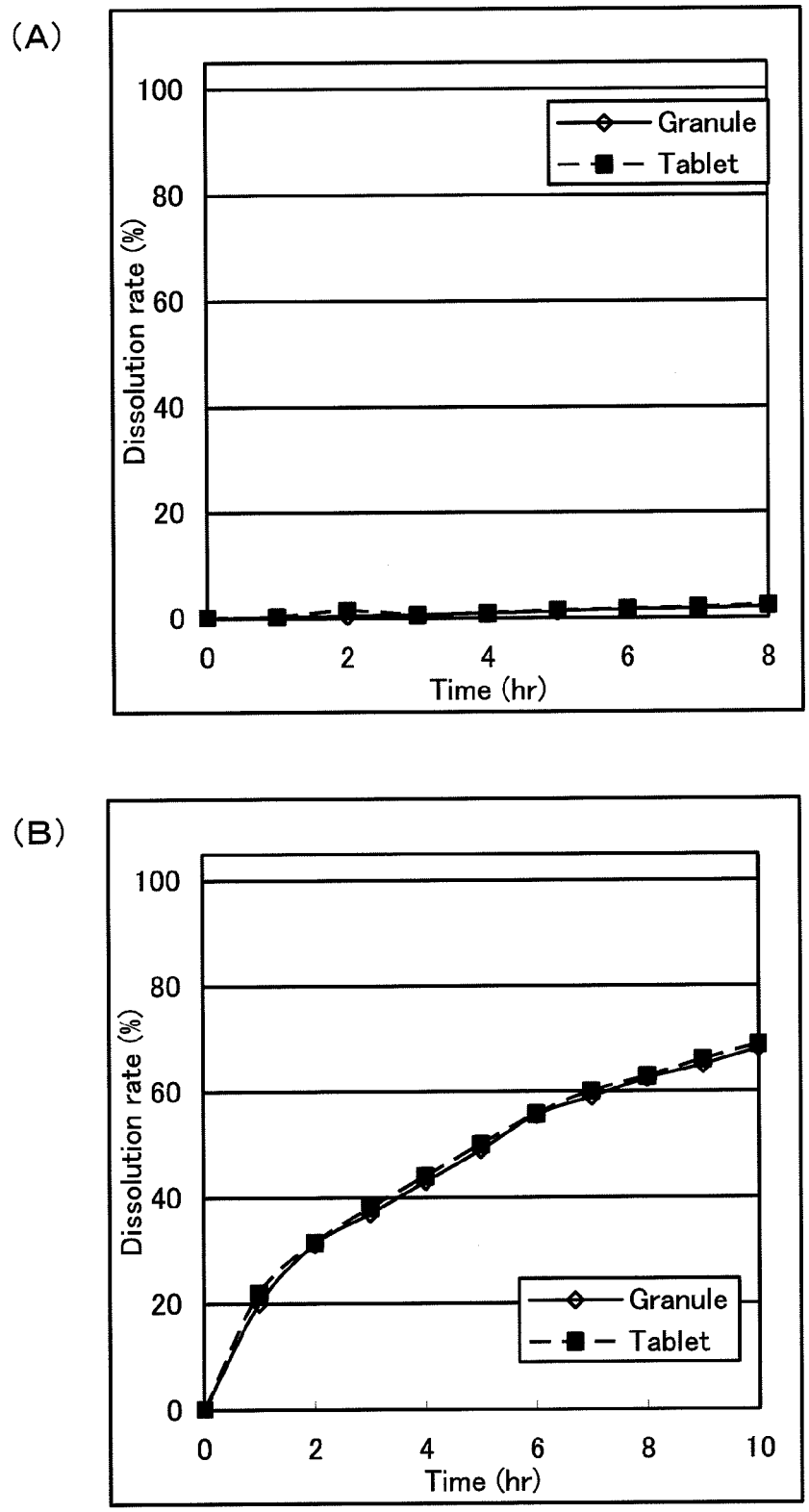
FIG. 13 is a graph showing the time-dependent changes in the drug dissolution rate of the granules and tablets prepared in Comparative Examples.

The 500 mg tablet [RT2] had riboflavin dissolution rates of 0.6% in the 1st fluid after 3 hours and 31.5% in the 2nd fluid after 2 hours, 41.1% after 4 hours, 55.7% after 6 hours, 62.8% after 8 hours and 68.9% after 10 hours. FIG. 13 shows the time-dependent changes in the drug dissolution rate of the granules and tablets. (A) shows the time-dependent changes in the drug dissolution rate in the 1st fluid and (B) shows the same in the 2nd fluid.

In Comparative Example 2, the film coating solution [RL2] was used wherein the blending ratio of the methacrylic acid copolymer LD [b] was 40 or lower to 100 of the ethyl acrylate/methyl methacrylate copolymer dispersion [a]. For this reason, the film coated granule [RF2] and the 500 mg tablet [RT2] consequently had delayed drug dissolutions in the 2nd fluid. Further, the film coating solution [RL2] had the composition wherein the ethyl acrylate/methyl methacrylate copolymer dispersion [a] was excessively contained and hence had a high adhesiveness, thereby causing many agglomerations.

Comparative Example 3

A film coating solution [RL4] having a solid content of 17 mass % was prepared in the same manner as in Example 2 except that the solid mass ratio of the blending components was a:b:c:d:e=40:35:15:0:10 (=100:87.5:37.5:0.25.0) and titanium oxide is not included. The tensile elongation of the cast film formed using the aqueous film coating solution [RL4] was 180%.

Next, a film coated granule [RF4] was produced in the same manner as in Example 1 except that the aqueous film coating solution [RL4] was used in place of the aqueous film coating solution [L1].

The coated film amount of the obtained film coated granule [RF4] was 20 mass %, and the average particle size was 438 μm (the film thickness was about 17.8 μm). The yield was 82.6% and the agglomeration rate (the ratio of coarse particles of 600 μm or larger) was 21.4%.

The film coated granule [RF4] had riboflavin dissolution rates of 2.2% in the 1st fluid after 3 hours and 68.9% in the 2nd fluid after 2 hours, 89.0% after 4 hours, 96.8% after 6 hours and 100% after 8 hours.

Subsequently, a 500 mg tablet [RT4] was produced in the same manner as in Example 1 except that the film coated granule [RF4] was used in place of the film coated granule [F1]. The obtained 500 mg tablet [RT4] had a tablet hardness of 170 N and an integration time of 95 seconds.

Figure 14:
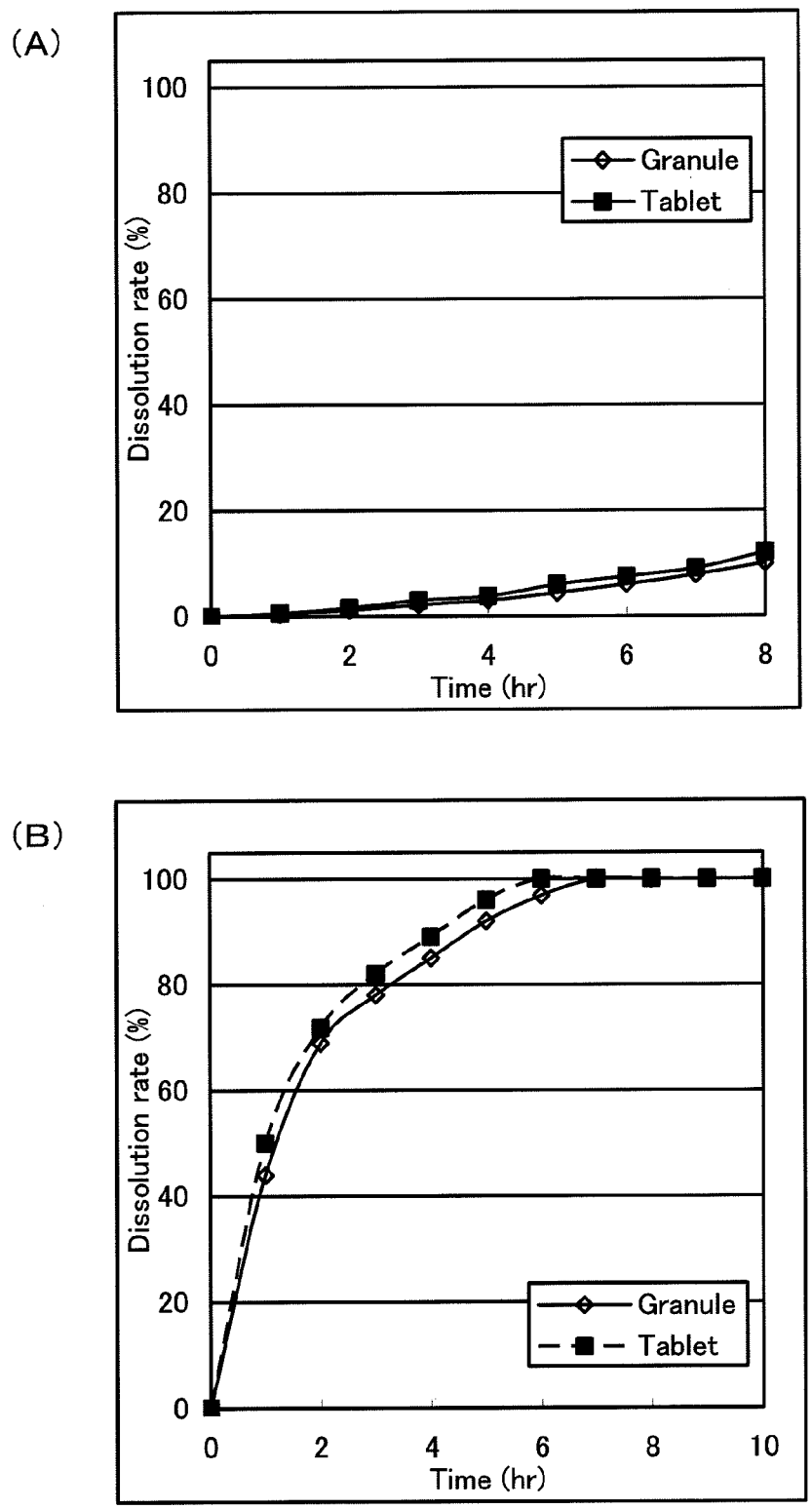
FIG. 14 is a graph showing the time-dependent changes in the drug dissolution rate of the granules and tablets prepared in Comparative Examples.

The 500 mg tablet [RT4] had riboflavin dissolution rates of 2.5% in the 1st fluid after 3 hours and 71.8% in the 2nd fluid after 2 hours, 82.1% after 4 hours, 100% after 6 hours and 100% after 8 hours. FIG. 14 shows the time-dependent changes in the drug dissolution rate of the granules and tablets. (A) shows the time-dependent changes in the drug dissolution rate in the 1st fluid and (B) shows the same in the 2nd fluid.

In Comparative Example 3, the film coating solution [RL4] used, with no titanium oxide contained, had a high adhesiveness and hence caused many agglomerations. Further, the film layer formed of the film coated granule [RF4] was non-uniform, thereby deteriorating the film properties, and the drug dissolution was consequently expedited.

Comparative Example 4

A film coating solution [RL5] having a solid content of 17 mass % was prepared in the same manner as in Example 2 except that the solid mass ratio of the blending components was a:b:c:d:e=40:45:3:3:9 (=100:112.5:7.5:7.5:22.5). The tensile elongation of the cast film formed using the aqueous film coating solution [RL5] was 128%.

Next, a film coated granule [RF5] was produced in the same manner as in Example 1 except that the film coating solution [RL5] was used in place of the aqueous film coating solution [L1].

The coated film amount of the obtained film coated granule [RF5] was 20 mass %, and the average particle size was 436 μm (the film thickness was about 16.8 μm). The yield was 96.9% and the agglomeration rate (the ratio of coarse particles of 600 μm or larger) was 6.2%.

The film coated granule [RF5] had riboflavin dissolution rates of 6.3% in the 1st fluid after 3 hours and 74.3% in the 2nd fluid after 2 hours, 97.1% after 4 hours and 100% after 6 hours.

Subsequently, a 500 mg tablet [RT5] was produced in the same manner as in Example 1 except that the film coated granule [RF5] was used in place of the film coated granule [F1]. The obtained 500 mg tablet [RT5] had a tablet hardness of 120 N and an integration time of 72 seconds.

Figure 15:
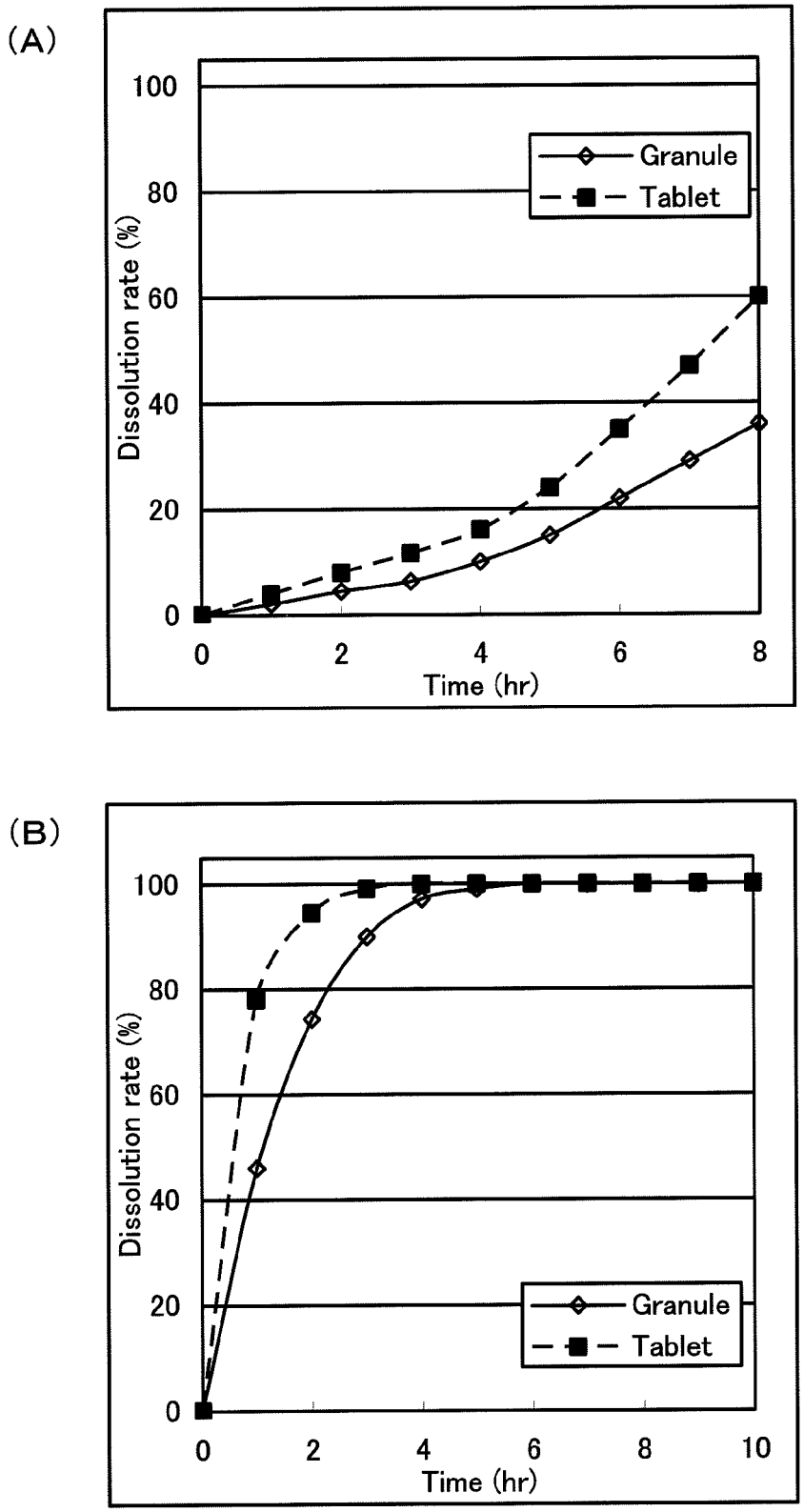
FIG. 15 is a graph showing the time-dependent changes in the drug dissolution rate of the granules and tablets prepared in Comparative Examples.

The 500 mg tablet [RT5] had riboflavin dissolution rates of 11.6% in the 1st fluid after 3 hours and 94.5% in the 2nd fluid after 2 hours, 100% after 4 hours and 100% after 6 hours. FIG. 15 shows the time-dependent changes in the drug dissolution rate of the granules and tablets. (A) shows the time-dependent changes in the drug dissolution rate in the 1st fluid and (B) shows the same in the 2nd fluid.

In Comparative Example 4, the film coating solution [RL1] was used wherein the blending ratio of the ethyl acrylate/methyl methacrylate copolymer dispersion [a] was lower than the methacrylic acid copolymer LD dispersion [b]. For this reason, the film coated granule [RF1] and the 500 mg tablet [RT1] had drug dissolutions of 3% or more in the 1st fluid after 3 hours. Further, the drug dissolutions were expedited before and after the tablet compression force which resulted in increased drug dissolutions of 3% or more.

Comparative Example 5

A film coating solution [RL6] having a solid content of 30 mass % was prepared in the same manner as in Example 6 except that the solid content was 30 mass %. The tensile elongation of the cast film formed using the aqueous film coating solution [RL6] was 215%.

Next, a film coated granule [RF6] was produced in the same manner as in Example 4 except that the film coating solution [RL6] was used in place of the aqueous film coating solution [L1].

The coated film amount of the obtained film coated granule [RF6] was 20 mass %, and the average particle size was 208 µm (the film thickness was about 21.0 µm). The yield was 81.2% and the agglomeration rate (the ratio of coarse particles of 600 µm or larger) was 35.8%.

In Comparative Example 5, the film coating solution [RL6] having a solid content of 30 mass % was used. For this reason, the film coating solution [RL6] had a high adhesiveness and hence caused the granules to attach to the inner walls and filters of the apparatus, thereby decreasing the yield. Further, the granules agglomerated to each other and increased the agglomeration rate, whereby the solution failed to achieve the practical production efficiency.

Comparative Example 6

Using talc [f] in place of the titanium oxide [d], a film coating solution [RL7] was prepared in the same manner as in Example 1 except that the solid mass ratio of the blending components was a:b:c:f=9.8:75.7:10.7:3.8 (=100:776:110:38.5) and a solid content was 20 mass %. The tensile elongation of the cast film formed using the aqueous film coating solution [RL7] was 15%.

Next, a film coated granule [RF7] was produced in the same manner as in Example 1 except that the film coating solution [RL7] was used in place of the aqueous film coating solution [L1].

The coated film amount of the obtained film coated granule [RF7] was 20 mass % and the average particle size was 445 µm (the film thickness was about 21.3 µm). The yield was 96.2% and the agglomeration rate (the ratio of coarse particles of 600 µm or larger) was 6.0%.

The film coated granule [RF7] had riboflavin dissolution rates of 0.5% in the 1st fluid after 3 hours and 100% in the 2nd fluid after 2 hours.

Subsequently, a 500 mg tablet [RT7] was produced in the same manner as in Example 1 except that the film coated granule [RF7] was used in place of the film coated granule [F1]. The obtained 500 mg tablet [RT7] had a tablet hardness of 110 N and an integration time of 65 seconds.

Figure 16:
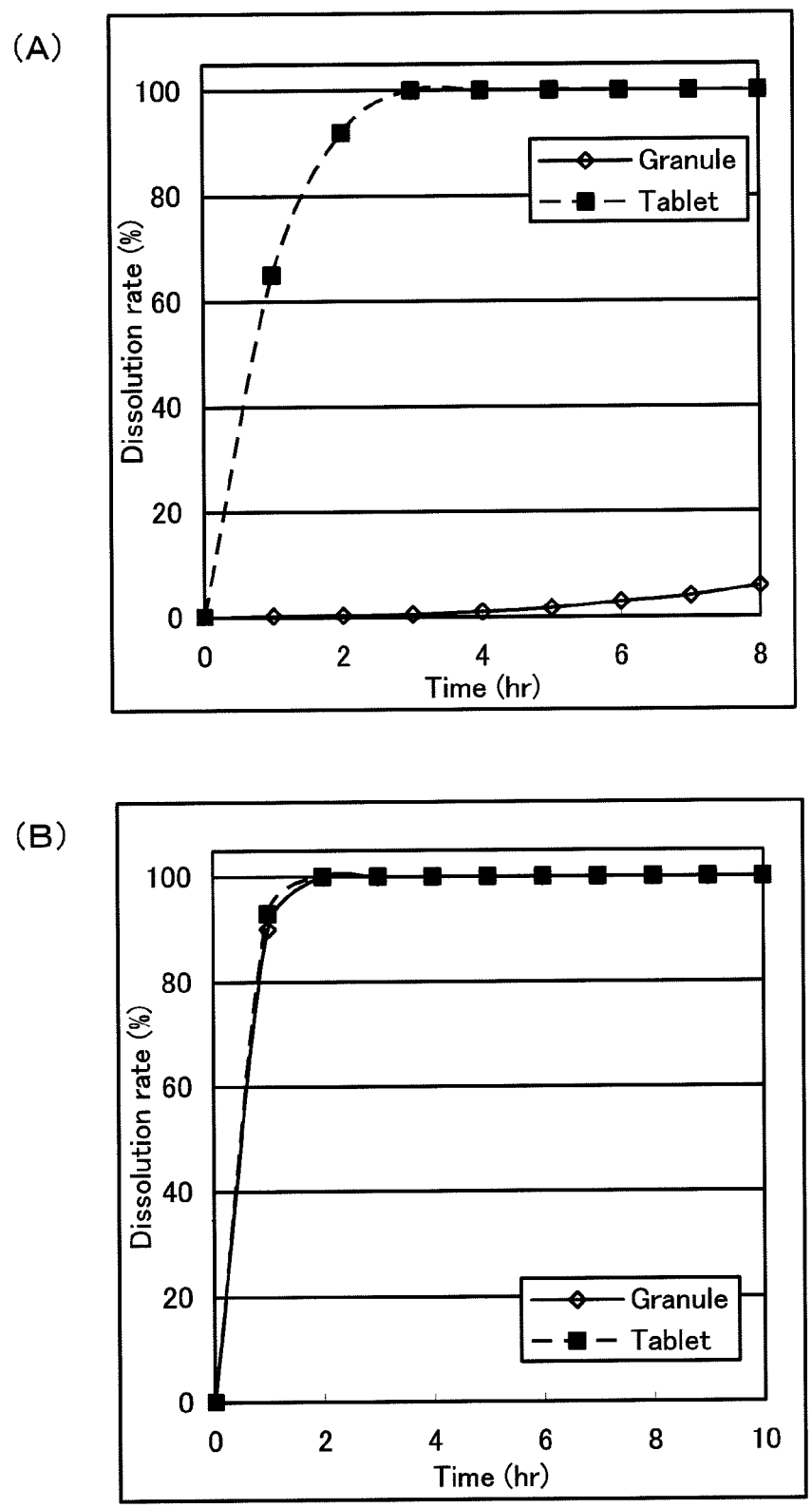
FIG. 16 is a graph showing the time-dependent changes in the drug dissolution rate of the granules and tablets prepared in Comparative Examples.

The 500 mg tablet [RT7] had riboflavin dissolution rates of 100% in the 1st fluid after 3 hours and 100% in the 2nd fluid after 2 hours. FIG. 16 shows the time-dependent changes in the drug dissolution rate of the granules and tablets. (A) shows the time-dependent changes in the drug dissolution rate in the 1st fluid and (B) shows the same in the 2nd fluid.

In Comparative Example 6, the film coating solution [RL7] was used wherein the blending ratio of the methacrylic acid copolymer LD dispersion [b] is 100 or higher to 100 of the ethyl acrylate/methyl methacrylate copolymer dispersion [a]. For this reason, talc was fully capable of exhibiting the effect to prevent the granules from agglomerating. However, the tensile elongation of the cast film remains 150% or less which caused film damages during the tablet compression force, consequently disabling the drug dissolution control.

Tables 1, 2, 3 and 4 show the results of Examples 1 to 11 and Comparative Examples 1 to 6.

TABLE 1

|  | Example 1 | Example 2 | Example 3 | Example 4 | Example 5 |
|---|---|---|---|---|---|
| Nuclear particle | CP-305 | CP-305 | CP-305 | CP-102 | CP-305 |
| [a] Ethyl acrylate/methyl methacrylate copolymer dispersion | 100 | 100 | 100 | 100 | 100 |
| [b] Methacrylic acid copolymer LD | 87.5 | 66.7 | 41.6 | 66.7 | 87.5 |
| [c] Triethyle citrate | 37.5 | 11.1 | 12.5 | 11.1 | 37.5 |
| [d] Titanium oxide | 25.0 | 22.2 | 12.5 | 22.2 | 25.0 |
| [e] Microparticulate methacrylic acid copolymer L | — | 22.2 | — | 22.2 | — |
| Film coating solution solid content | 17 | 17 | 17 | 17 | 5 |
| Cast film tensile elongation | 199% | 213% | 443% | 213% | 180% |
| Average particle size | 443 µm | 449 µm | 454 µm | 201 µm | 440 µm |
| Yield | 90.7% | 94.4% | 92.8% | 92.8% | 93.50% |
| Agglomeration rate | 8.8% | 6.8% | 10.2% | 7.8% | 1.7% |
| Granule: $1^{st}$ fluid/3 hr dissolution | 1.8% | 0.8% | 0.7% | 1.9% | 1.5% |
| Granule: $2^{nd}$ fluid/4 hr dissolution | 96.3% | 78.8% | 61.5% | 87.6% | 95.1% |
| Tablet hardness | 150N | 168N | 225N | 195N | 155N |
| Disintegration time | 75 sec | 89 sec | 125 sec | 112 sec | 70 sec |
| Tablet: $1^{st}$ fluid/3 hr dissolution | 1.9% | 1.2% | 0.8% | 2.1% | 1.6% |
| Tablet: $2^{nd}$ fluid/4 hr dissolution | 97.5% | 80.8% | 62.1% | 90.5% | 96.3% |

TABLE 2

|  | Example 6 | Example 7 | Example 8 | Example 9 | Example 10 | Example 11 |
|---|---|---|---|---|---|---|
| Nuclear particle | CP-102 | CP-305 | CP-305 | CP-305 | CP-305 | CP-305 |
| [a] Ethyl acrylate/methyl methacrylate | 100 | 100 | 100 | 100 | 100 | 100 |

TABLE 2-continued

|  | Example 6 | Example 7 | Example 8 | Example 9 | Example 10 | Example 11 |
|---|---|---|---|---|---|---|
| copolymer dispersion |  |  |  |  |  |  |
| [b] Methacrylic acid copolymer LD | 66.7 | 87.5 | 42 | 87.5 | 87.5 | 62.5 |
| [c] Triethyle citrate | 11.1 | 37.5 | 7 | 46 | 37.5 | 12.5 |
| [d] Titanium oxide | 22.2 | 7 | 25 | 25 | 25.0 | 25.0 |
| [e] Microparticulate methacrylic acid copolymer L | 22.2 | — | 12 | — | — | 50.0 |
| Film coating solution solid content | 20 | 17 | 17 | 17 | 17 | 17 |
| Cast film tensile elongation | 210% | 245% | 410% | 165% | 199% | 118% |
| Average particle size | 206 μm | 444.4 μm | 464 μm | 430 μm | 450 μm | 461 μm |
| Yield | 90.1% | 88.2% | 90.5% | 96.8% | 87.8% | 93.8% |
| Agglomeration rate | 10.8% | 11.6% | 13.0% | 1.5% | 9.7% | 5.5% |
| Granule: $1^{st}$ fluid/3 hr dissolution | 1.9% | 1.1% | 0.9% | 1.0% | 2.4% | 7.2% |
| Granule: $2^{nd}$ fluid/4 hr dissolution | 86.9% | 94.7% | 75.3% | 96.7% | 100.0% | 96.4% |
| Tablet hardness | 191 N | 175N | 200N | 120N | 125N | 138N |
| Disintegration time | 120 sec | 90 sec | 110 sec | 65 sec | 60 sec | 92 sec |
| Tablet: $1^{st}$ fluid/3 hr dissolution | 2.0% | 1.3% | 1.8% | 1.6% | 2.9% | 10.8% |
| Tablet: $2^{nd}$ fluid/4 hr dissolution | 89.4% | 96.5% | 77.9% | 98.3% | 100.0% | 100.0% |

TABLE 3

|  | Comparative Example 1 | Comparative Example 2 | Comparative Example 3 |
|---|---|---|---|
| Nuclear particle | CP-305 | CP-305 | CP-305 |
| [a] Ethyl acrylate/methyl methacrylate copolymer dispersion | 100 | 100 | 100 |
| [b] Methacrylic acid copolymer LD | 150 | 30.7 | 87.5 |
| [c] Triethyle citrate | 23.3 | 7.8 | 37.5 |
| [d] Titanium oxide | 26.7 | 15.4 | 0.0 |
| [e] Microparticulate methacrylic acid copolymer L | 33.3 | — | 25.0 |
| Film coating solution solid content | 17 | 17 | 17 |
| Cast film tensile elongation | 94% | 650% | 180% |
| Average particle size | 438 μm | 458 μm | 438 μm |
| Yield | 94.3% | 78.6% | 82.6% |
| Agglomeration rate | 6.8% | 29.5% | 21.4% |
| Granule: $1^{st}$ fluid/3 hr dissolution | 7.2% | 0.6% | 2.2% |
| Granule: $2^{nd}$ fluid/4 hr dissolution | 98.0% | 43.0% | 89.0% |
| Tablet hardness | 126N | 185N | 170N |
| Disintegration time | 75 sec | 180 sec | 95 sec |
| Tablet: $1^{st}$ fluid/3 hr dissolution | 13.3% | 0.6% | 2.5% |
| Tablet: $2^{nd}$ fluid/4 hr dissolution | 100.0% | 41.1% | 82.1% |

TABLE 4

|  | Comparative Example 4 | Comparative Example 5 | Comparative Example 6 |
|---|---|---|---|
| Nuclear particle | CP-305 | CP-102 | CP-305 |
| [a] Ethyl acrylate/methyl methacrylate copolymer dispersion | 100 | 100 | 100 |
| [b] Methacrylic acid copolymer LD | 112.5 | 66.7 | 778 |
| [c] Triethyle citrate | 7.5 | 11.1 | 33.3 |
| [d] Titanium oxide | 7.5 | 22.2 | (Talc) 11.6 |
| [e] Microparticulate methacrylic acid copolymer L | 22.5 | 22.2 | — |
| Film coating solution solid content | 17 | 30 | 20 |
| Cast film tensile elongation | 128% | 215% | 15% |
| Average particle size | 436 μm | 208 μm | 445 μm |
| Yield | 96.9% | 81.2% | 96.2% |
| Agglomeration rate | 6.2% | 35.8% | 6.0% |
| Granule: $1^{st}$ fluid/3 hr dissolution | 6.3% | — | 0.5% |
| Granule: $2^{nd}$ fluid/4 hr dissolution | 97.1% | — | 100.0% |
| Tablet hardness | 120N | — | 110N |
| Disintegration time | 72 sec | — | 65 sec |
| Tablet: $1^{st}$ fluid/3 hr dissolution | 11.6% | — | 100.0% |
| Tablet: $2^{nd}$ fluid/4 hr dissolution | 100.0% | — | 100.0% |

This application is based on the Japanese Patent Application (Patent Application No. 2007-297666) filed on Nov. 16, 2007, and the content thereof is incorporated herein by reference.

Industrial Applicability

The present invention achieves the production of a film coating having good acid resistance and sustained release properties as well as flexibility suitable for the tablet compression force without developing excessive adhesiveness, and being highly productive and cost efficient. Accordingly, the film is widely and effectively applicable in the use of the film coatings, which require acid resistance and sustained release properties. In particular, the present invention can provide a film coating solution, a granule coated with the coating solution and a tablet containing such a film coated granule suitably applicable in the field of drug containing enteric sustained release preparations.

The invention claimed is:

1. An aqueous film coating solution comprising an ethyl acrylate/methyl methacrylate copolymer dispersion, a methacrylic acid copolymer LD, a plasticizer, titanium oxide and water, wherein the solid mass ratio of the ethyl acrylate/methyl methacrylate copolymer dispersion, the methacrylic acid copolymer LD, the plasticizer and the titanium oxide is 100:(40 to 100):(5 to 50):(5 to 30) and the solid content is 5 to 20 mass%, and wherein a tensile elongation of a cast film formed using the aqueous film coating solution is from 150% to 443%.

2. The aqueous film coating solution according to claim 1, further comprising one or more enteric polymers selected from the group consisting of methacrylic acid copolymer L, hydroxypropyl methylcellulose phthalate acetate succinate, carboxy methyl ethyl cellulose, hydroxypropyl methylcellulose phthalate, and cellulose acetate phthalate.

3. The aqueous film coating solution according to claim 2 wherein the solid mass ratio of the ethyl acrylate/methyl methacrylate copolymer dispersion, the methacrylic acid copolymer LD, the plasticizer, the titanium oxide and the enteric polymer other than the methacrylic acid copolymer LD is 100:(40 to 100):(5 to 50):(5 to 30):(more than 0 and not more than 30).

4. The aqueous film coating solution according to claim 2, wherein the average particle size of the enteric polymer is 25 μm or less.

5. The aqueous film coating solution according to claim 2, wherein the enteric polymer comprises a methacrylic acid copolymer L.

6. The film coating solution according to claim 1, wherein the plasticizer is one or more selected from the group consisting of triethyl citrate, triacetin, glycerin, dibutyl phthalate and propylene glycol.

7. A film coated granule comprising an elementary granule comprising a drug and a coating layer covering the external surface of the elementary granule, wherein the coating layer comprises an ethyl acrylate/methyl methacrylate copolymer, a methacrylic acid copolymer LD, a plasticizer and titanium oxide, and the solid mass ratio of the ethyl acrylate/methyl methacrylate copolymer, the methacrylic acid copolymer LD, the plasticizer and the titanium oxide is 100:(40 to 100):(5 to 50):(5 to 30), and wherein a tensile elongation of a cast film formed using the aqueous film coating solution is from 150% to 443%.

8. The film coated granule according to claim 7, wherein the coating layer further comprises one or more enteric polymers selected from the group consisting of methacrylic acid copolymer L, hydroxypropyl methylcellulose phthalate acetate succinate, carboxy methyl ethyl cellulose, hydroxypropyl methylcellulose phthalate, and cellulose acetate phthalate.

9. The film coated granule according to claim 8 wherein the solid mass ratio of the ethyl acrylate/methyl methacrylate copolymer, the methacrylic acid copolymer LD, the plasticizer, the titanium oxide and the enteric polymer other than the methacrylic acid copolymer LD is 100:(40 to 100):(5 to 50):(5 to 30):(more than 0 and not more than 30).

10. The film coated granule according to claim 7, wherein the plasticizer is one or more selected from the group consisting of triethyl citrate, triacetin, glycerin, dibutyl phthalate and propylene glycol.

11. The film coated granule according to claim 7, wherein the elementary granule comprises a spherical nuclear particle comprising 70 mass% or more of crystalline cellulose.

12. A tablet containing the film coated granule of claim 7.

* * * * *